US009932410B2

(12) United States Patent
Poul et al.

(10) Patent No.: US 9,932,410 B2
(45) Date of Patent: Apr. 3, 2018

(54) HUMAN NEUTRALIZING ANTI-KIT ANTIBODIES AND USES THEREOF

(71) Applicants: INSERM (Institut National de la Sante et de la Recherche Medicale), Paris (FR); Centre National de la Recherche Scientifique (CNRS), Paris (FR); Universite de Montpellier, Montpellier (FR); Universite Paris-Sud, Orsay (FR); Institut Regional du Cancer de Montpellier, Montpellier (FR); Ecole Normale Superieure de Cachan, Cachan (FR)

(72) Inventors: Marie-Alix Poul, Montpelier (FR); Mariane Le Gall, Montpelier (FR); Ronan Crepin, Cachan (FR)

(73) Assignees: INSERM (Institut National de la Sante et de la Recherche Medicale, Paris (FR); Centre National de la Recherche Scientifique (CNRS), Paris (FR); Universite de Montpellier, Montpellier (FR); Universite Paris-Sud, Orsay (FR); Institut Regional du Cancer du Montpellier, Montpellier (FR); Ecole Normale Superieure de Cachan, Cachan (FR)

( * ) Notice: Subject to any disclaimer, the term of this patent is extended or adjusted under 35 U.S.C. 154(b) by 0 days.

(21) Appl. No.: 15/034,350

(22) PCT Filed: Nov. 5, 2014

(86) PCT No.: PCT/EP2014/073835
§ 371 (c)(1),
(2) Date: May 4, 2016

(87) PCT Pub. No.: WO2015/067667
PCT Pub. Date: May 14, 2015

(65) Prior Publication Data

US 2016/0264680 A1 Sep. 15, 2016

(30) Foreign Application Priority Data

Nov. 5, 2013 (EP) .................................... 13306519

(51) Int. Cl.
*C07K 16/40* (2006.01)
*C07K 16/18* (2006.01)
*C07K 16/28* (2006.01)
*C07K 16/30* (2006.01)

(52) U.S. Cl.
CPC .......... *C07K 16/40* (2013.01); *C07K 16/2803* (2013.01); *C07K 16/28* (2013.01); *C07K 2317/21* (2013.01); *C07K 2317/33* (2013.01); *C07K 2317/35* (2013.01); *C07K 2317/52* (2013.01); *C07K 2317/56* (2013.01); *C07K 2317/565* (2013.01); *C07K 2317/622* (2013.01); *C07K 2317/73* (2013.01); *C07K 2317/76* (2013.01); *C07K 2317/77* (2013.01); *C07K 2317/92* (2013.01); *C07K 2319/00* (2013.01)

(58) Field of Classification Search
None
See application file for complete search history.

(56) References Cited

U.S. PATENT DOCUMENTS

2011/0311538 A1* 12/2011 Schlessinger ...... C07K 16/2803 424/138.1
2012/0189633 A1 7/2012 Yaron et al.

FOREIGN PATENT DOCUMENTS

WO 2007/127317 A2 11/2007
WO 2011/119948 A1 9/2011
WO 2012/154480 A1 11/2012

OTHER PUBLICATIONS

Padlan, Advances in Protein Chemistry, 1996, 49:57-133.*
Berglund, Berglund et al, Protein Science, 2008, 17:606-613.*
Yoshida et al.; "Therapeutic Efficacy of C-Kit-Targeted Radioimmunotherapy Using 90Y-Labeled Anti-C-Kit Antibodies in a Mouse Model of Small Cell Lung Cancer"; PLOS One, vol. 8, No. 3, Mar. 14, 2013, pp. 1-8.
Reshetnyak et al.; "Structural basis for Kit receptor tyrosine kinase inhibition by antibodies targeting the D4 membrane-proximal region"; Proceedings of the National Academy of Sciences, vol. 110, No. 44, Oct. 14, 2013, pp. 17832-17837.
Reshetnyak et al.; "Structural basis for Kit receptor tyrosine kinase inhibition by antibodies targeting the D4 membrane-proximal region—Supporting Information"; Proceedings of the National Academy of Sciences, vol. 110, No. 14, Oct. 14, 2013, pp. 17832-17837.
Edris et al.; "Anti-Kit monoclonal antibody inhibits imatinib-resistant gastrointestinal stromal tumor growth"; Proceedings of the National Academy of Sciences of the United States of America, vol. 110, No. 9, Feb. 26, 2013, pp. 3501-3506.

* cited by examiner

*Primary Examiner* — Hong Sang
(74) *Attorney, Agent, or Firm* — Whitham Curtis & Cook, PC

(57) ABSTRACT

The invention relates to human neutralizing anti-KIT antibodies and uses thereof. More particularly, the invention relates to an antibody comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region. The invention also relates to an antibody comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 14 in the L-CDR1 region, SEQ ID NO: 15 in the L-CDR2 region and SEQ ID NO: 16 in the L-CDR3 region.

14 Claims, 8 Drawing Sheets

Figure 1:
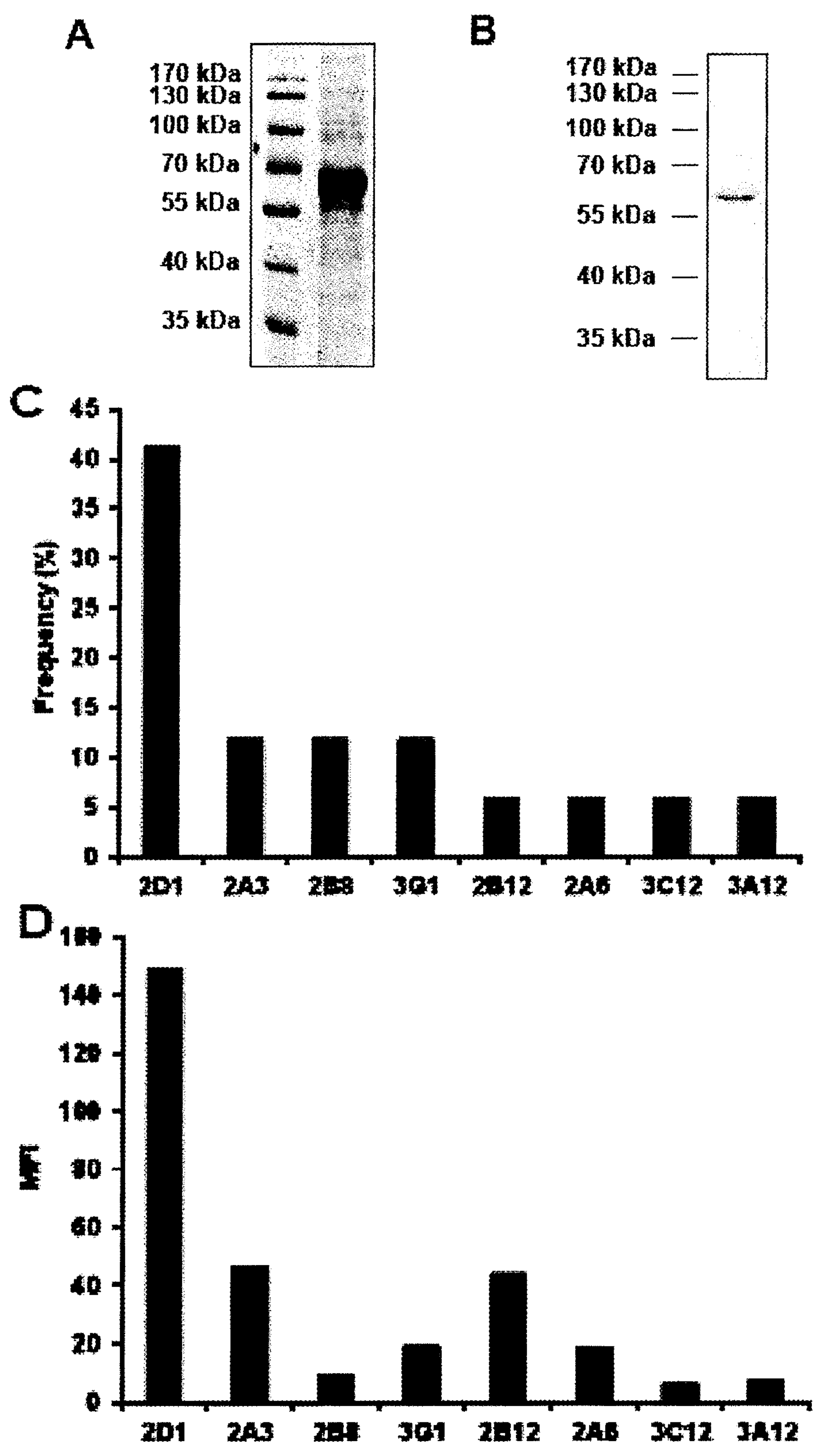

| | ka (1/Ms) | kd (1/s) | KA (1/M) | KD(M) |
|---|---|---|---|---|
| 2D1 | $(3.22+/-0.5)x10^{4}$ | $(5.63+/-0.07)x10^{-3}$ | $5.79x10^{6}$ | $1.73x10^{-7}$ |
| 3G1 | $(7.81+/-0.07)x10^{4}$ | $(5.21+/-0.04)x10^{-3}$ | $1.5x10^{7}$ | $6.67x10^{-8}$ |

HUMAN NEUTRALIZING ANTI-KIT ANTIBODIES AND USES THEREOF

CROSS REFERENCE TO RELATED APPLICATIONS

This application is a National Stage Application based on the International Application No. PCT/EP2014/073835 filed Nov. 5, 2014 which claims priority to European Application 13306519.3 filed Nov. 5, 2013.

SEQUENCE LISTING

This document incorporates by reference an electronic sequence listing text file, which was electronically submitted along with this document. The text file is named Sequence-Listing.txt, is 20 kilobytes, and was created on May 4, 2016.

FIELD OF THE INVENTION

The invention relates to human neutralizing anti-KIT antibodies and uses thereof.

BACKGROUND OF THE INVENTION

KIT is a 145 kD type III tyrosine kinase receptor that functions as a growth factor receptor. KIT ligand is the Stem Cell Factor (SCF) (Roskoski 2005). Type III tyrosine kinase receptors are characterized by the presence of five N-glycosylated immunoglobulin domains in the extra-cellular region and by a split tyrosine kinase intra-cellular domain. The first three extra-cellular domains (D1-3) are involved in the binding of SCF (Lev, Blechman et al. 1993) while the fourth (D4) and fifth (D5) domains are implicated in receptor dimerization following SCF binding (Blechman and Yarden 1995). The intracellular region of KIT contains the catalytical domain composed of the ATP binding site and the phosphotransferase domain. KIT stimulation by SCF induces its dimerization and autophosphorylation which activates downstream effector proteins including the phosphoinositide 3-kinase (PI3K)/AKT, phospholipase C, signal transducer and activator of transcription (STAT) and RAS/MAP-kinase pathways (Roskoski 2005). SCF is a major cytokine for the self-renewal, proliferation and differentiation of hematopoietic lineage, germ cells, melanocytes, gut and central nervous system in embryo (Orr-Urtreger, et al. 1990). In adult mice KIT is expressed in a limited number of tissues and KIT defects induce impaired hematopoïesis, decreased numbers of tissue mast cells, decreased fertility and pigmentation, and defective development of the interstitial cells of Cajal, which are responsible for intestinal pacemaker activity (for review see Broudy 1997).

Abnormal KIT signalling is observed in cancer due either to overexpression SCF and/or KIT itself or to activating mutations that render KIT signalling independent of SCF. These mutations of KIT are major oncogenic drivers in gastrointestinal stromal tumours (GIST) (Demetri, von Mehren et al. 2002), that derive from Cajal cells, in subsets of acute myeloid leukemia (Core-binding factor acute myeloid leukemia CBF-AML) (Wang, Zhao et al. 2011) and melanoma (Hodi, Corless et al. 2013) and less frequently, in other cancers. Consequently, oncogenic KIT inhibition with tyrosine kinase inhibitors has proven successful in those pathologies (for review, Lennartsson and Ronnstrand 2012). Un-mutated KIT, is also involved in a number of malignant diseases derived from cell-types that generally expressed KIT transiently during embryogenesis (Bernex, De Sepulveda et al. 1996). The SCF/KIT axis functions as an autocrine or paracrine loop sustaining cancer cells to proliferate and/or to migrate. Indeed, KIT is present on 50% of AML (Ikeda, Kanakura et al. 1991) and AML blasts frequently respond to SCF stimulation by increased proliferation (Pietsch et al., 1992). Consistently, cases of AML patients, refractory to chemotherapy, can be cured by TKI (Xiang, Kreisel et al. 2007). A number of solid tumours also frequently express KIT and/or SCF including small cell lung cancer (SCLC), melanoma, semimoma (Went, Dirnhofer et al. 2004). Typically, seventy % of SCLC co-express SCF and KIT (Hibi, Takahashi et al. 1991; Rygaard, Nakamura et al. 1993; Krystal, Hines et al. 1996) and high KIT levels are associated with a poor prognosis (Micke, Basrai et al. 2003) while KIT kinase inhibitor Imatinib decreases cancer cell proliferation in vitro (Krystal, Honsawek et al. 2000) and reduces SCF-dependent VEGF secretion (Litz and Krystal 2006). Small cell lung cancer (NSCLC), also frequently express KIT (Yoo, Kim et al. 2004) and interestingly, Imatinib or SCF-blocking mAbs eliminate NSCLC cancer stem cell sub-population (Levina, Marrangoni et al. 2010). Other solid tumours have been reported to express KIT including breast cancers (Hines et al., 1995), neuroblastomas (Cohen et al., 1994), colon cancers (Toyota et al., 1994), gynecological tumours (Inoue et al., 1994), and gliomas (Stanulla et al., 1995).

Pharmacologic inhibition of KIT is a potential approach to treat malignancies that are partly or completely dependent on the activity of KIT receptor. ATP-competitive tyrosine kinase inhibitors like Imatinib (Heinrich, Griffith et al. 2000) or Dasatinib (Schittenhelm, Aichele et al. 2003) inhibit KIT phosphorylation and interfere with cell growth or survival. Unfortunately, a number KIT mutations located in the activating loop exhibits resistance to Imatinib in the clinic (Zermati, De Sepulveda et al. 2003; Ma, Mali et al. 2012) and initially Imatinib sensitive regulatory mutants accumulate secondary mutations leading to patient resistance to treatment (Antonescu, Besmer et al. 2005).

Because of their high specificity and high binding affinity combined to their natural ability to recruit immune effectors, monoclonal antibodies (mAbs) (Adams and Weiner 2005) offer an attractive approach to target oncogenic KIT. Thus, recently an anti-KIT mAb (SR-1, initially disclosed in the International Patent Application WO92/17505) was reported to limit tumour progression by a macrophage-dependent mechanism in a mouse model of GIST (Edris, Willingham et al. 2013) and a radiolabelled anti-KIT antibody (12A8 mAb) was shown to decrease SCLC progression in mouse models (Yoshida, Tsuji et al. 2013). Antibody SR1 has been shown to inhibit SCF binding to KIT and SCF inhibits SR1 binding to KIT (Ashman, Buhring, et al. 1994). Additionally, monoclonal antibodies targeting Domain 4 of KIT have been described to neutralize KIT dependant cell growth by inhibition of homotypic D4 interactions essential for KIT activation (Reshetnyak, Nelson et al. 2013).

Recently, monoclonal antibodies that specifically target the extracellular domain (ECD) of human c-KIT have been disclosed (International patent application N° WO2012/154480). These monoclonal antibodies that specifically target the ECD of human c-KIT, including the CK6 antibody) are presented as capable of inducing internalization and/or degradation of plasma membrane bound c-KIT without inducing c-KIT agonist activities in tumor cells. However, the results disclosed in said patent application are in contradiction with this assertion since anti-c-KIT mAb CK6 is not observed as significantly inducing degradation of c-KIT expressed by GIST882 human tumor cells, expressed by Mo7e human tumor cells and expressed by Malm-3M human tumor cells in a time-dependent manner.

Therefore, until now, no monoclonal antibodies capable of inducing internalization and degradation of oncogenic forms of KIT have been described. Moreover, no neutralizing antibody binding to D5 of KIT has been yet described.

SUMMARY OF THE INVENTION

The invention relates to an isolated human neutralizing antibody that binds to KIT, which further induces internalization and degradation of oncogenic forms of KIT.

The invention thus relates to an antibody comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region. The invention also relates to an antibody comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 14 in the L-CDR1 region, SEQ ID NO: 15 in the L-CDR2 region and SEQ ID NO: 16 in the L-CDR3 region. The invention also relates to an antibody comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 27 in the L-CDR1 region, SEQ ID NO: 28 in the L-CDR2 region and SEQ ID NO: 29 in the L-CDR3 region. The invention also relates to an antibody comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 31 in the L-CDR1 region, SEQ ID NO: 32 in the L-CDR2 region and SEQ ID NO: 33 in the L-CDR3 region.

DETAILED DESCRIPTION OF THE INVENTION

The invention is based on the generation and characterization of two neutralizing scFv-Fc which interfered with SCF binding and consequently, inhibited SCF-dependant KIT phosphorylation and downstream signalling. These properties translated into a functional effect since these antibodies reduced the viability of the SCF-dependant KIT wild type expressing erythroleukemic cell line UT-7, after 3 days of treatment.

Interestingly, these anti-KIT scFv-Fc also reduced cell viability of two mast cell leukemia cell lines bearing activating mutations of KIT, including the HMC1.1 Imatinib sensitive cell line (with a V560G KIT activation mutation) and the HMC1.2 imatinib resistant cell line (with a V560G/D816V KIT activating mutation). Inhibition was due to intensive internalization and degradation of oncogenic forms of KIT upon antibody treatment.

These both monoclonal antibodies (referred as 2D1 and 3G1) likely inhibit KIT wild type KIT signaling by inhibition of homotypic interactions between the membrane-proximal domain of KIT-D5 after binding of SCF, that are crucial for receptor activation. The targeting of KIT-D5 by 2D1 and 3G1 induces the internalization of both wild type and oncogenic KIT and the degradation of oncogenic KIT while sparing WT KIT. Interestingly, internalization of KIT was thus observed independently of a wild type or mutated context (either catalytic or juxta membrane mutant) but strong degradation was observed only in mutant backgrounds.

These fully human antibodies thus represent new therapeutic tools useful for targeting diseases associated with KIT or SCF overexpression as well as for targeting oncogenic KIT signalling in cancer such as AML or GIST, and to bypass TKI resistance of certain mutants.

Definitions

The term "KIT" has its general meaning in the art and refers to the human KIT. KIT is also known as "kit", "c-kit", "CD117" or "stem cell factor receptor". The term "KIT" refers to both the natural and recombinant versions of the human natural KIT protein. The term thus includes naturally occurring KIT and variants and modified forms thereof. KIT is a cell surface type III tyrosine kinase receptor implicated in cancer through overexpression or oncogenic mutations that renders the kinase constitutively active. KIT ligand, the stem cell factor (SCF), triggers receptor homodimerization and phosphorylation and activates downstream effector pathways involved in cell survival, proliferation, homing or differenciation, depending on the cell type. KIT signalling is involved in leukemia and gastrointestinal stromal tumours (GIST). An exemplary native KIT amino acid sequence is provided in the UniProtKB/Swiss-Prot under accession number P10721).

The term "oncogenic forms of KIT", as used herein, refers to mutants of KIT with activating mutations, independently of SCF, resulting in the transduction of a constitutive signal that drives tumor growth and progression. Two groups of KIT activating mutations exist in cancer: regulation type mutations such as KIT V560G in GIST and enzymatic type mutations such as KIT D816V in acute myeloid lymphoma (AML).

The term "anti-KIT antibody" refers to an antibody directed against KIT.

According to the invention, the terms "antibody" or "immunoglobulin" have the same meaning, and will be used equally in the invention. The term "antibody" as used herein refers to immunoglobulin molecules and immunologically active portions of immunoglobulin molecules, i.e., molecules that contain an antigen binding site that immunospecifically binds an antigen. As such, the term antibody encompasses not only whole antibody molecules, but also antibody fragments as well as variants (including derivatives) of antibodies and antibody fragments. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

As used herein, the terms "neutralizing antibody" refers to an antibody that blocks or reduces at least one activity of a polypeptide comprising the epitope to which the antibody specifically binds. A neutralizing antibody reduces an activity in vitro and/or in vivo. Typically, a neutralizing antibody blocks Stem Cell Factor (SCF) binding to KIT and thus inhibits SCF induced activation of KIT. Accordingly, a neutralizing antibody inhibits SCF-induced KIT phosphorylation and then the KIT downstream signalling (which can be assessed by a phosphorylation assay for instance assessing the phosphorylation of KIT on tyrosines 568, 570 and/or 823 and/or the phosphorylation of AKT and ERK assay as described below).

As used herein, the term "Fab" denotes an antibody fragment having a molecular weight of about 50,000 and antigen binding activity, in which about a half of the N-terminal side of H chain and the entire L chain, among fragments obtained by treating IgG with a protease, papaine, are bound together through a disulfide bond.

As used herein, the term "F(ab')2" refers to an antibody fragment having a molecular weight of about 100,000 and antigen binding activity, which is slightly larger than the Fab bound via a disulfide bond of the hinge region, among fragments obtained by treating IgG with a protease, pepsin.

As used herein, the term "Fab'" refers to an antibody fragment having a molecular weight of about 50,000 and antigen binding activity, which is obtained by cutting a disulfide bond of the hinge region of the F(ab')2.

As used herein, the term "single chain Fv" ("scFv") polypeptide is a covalently linked VH::VL heterodimer which is usually expressed from a gene fusion including VH and VL encoding genes linked by a peptide-encoding linker.

As used herein, the term "dsFv" is a VH::VL heterodimer stabilised by a disulfide bond. Divalent and multivalent antibody fragments can form either spontaneously by association of monovalent scFvs, or can be generated by coupling monovalent scFvs by a peptide linker, such as divalent sc(Fv)2.

As used herein, the term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites.

By "purified" and "isolated" it is meant, when referring to an antibody according to the invention or to a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the polypeptide; however, the molecule may include some additional bases or moieties which do not deleteriously affect the basic characteristics of the composition.

Antibodies of the Invention:

The invention provides for isolated anti-KIT antibodies or fragments thereof.

In a first aspect, the invention thus relates to an isolated human neutralizing antibody that binds to KIT, which further induces internalization and degradation of oncogenic forms of KIT. More particularly, the invention relates to an isolated human neutralizing antibody that binds to KIT, which further induces internalization of KIT and only induces degradation of oncogenic forms of KIT.

In one embodiment, the invention relates to an isolated human neutralizing antibody that binds to the KIT domain D5 (as defined SEQ ID NO: 25), which further induces internalization and degradation of oncogenic forms of KIT.

| KIT-D5 Domain | Sequence |
|---|---|
| | NKPEILTYDRLVNGMLQCVAAGFPEPTIDWYFCPGTEQRCSA SVLPVDVQTLNSSGPPFGKLVVQSSIDSSAFKHNGTVECKAY NDVGKTSAYFNFAFKEQIHPHT (SEQ ID NO: 25) |

In particular, the inventors have isolated by antibody phage display two fully human anti-KIT single-chain variable antibody fragment (scFv), selected on a recombinant form of the extracellular domain of KIT referred as 2D1 and 3G1.

The inventors have cloned and characterized the variable domain of the light and heavy chains of said scFv 2D1, and thus determined the complementary determining regions (CDRs) domain of said antibody as described in Table 1:

| ScFv 2D1 Domains | Sequence |
|---|---|
| VH | MAQVKLQESGGGLVQPGGSLRLSCAAS**GFTFDSYA**MSWVRQA PGKGLEWVSY**ITSSSSTI**YYVDSVKGRFTISRDNAKNSLYLQ MNSLRDEDTAVYYCA**RLRNSEGYWYFDL**WGRGTLVTVSS (SEQ ID NO: 1) |
| H-CDR1 | GFTFDSYA (SEQ ID NO: 2) |
| H-CDR2 | ITSSSSTI (SEQ ID NO: 3) |
| H-CDR3 | RLRNSEGYWYFDL (SEQ ID NO: 4) |
| VL | SQSALTQDPAVSVALGQTVRITCQGD**SLRSYF**ASWYQQKPGQ APLLVMY**GQN**IRPSGIPDRFSGSSSGNSASLTITGAQAEDEA DYYC**NSRDSSYNHWV**FGGGTKLTVLG (SEQ ID NO: 5) |
| L-CDR1 | SLRSYF (SEQ ID NO: 6) |
| L-CDR2 | GQN (SEQ ID NO: 7) |
| L-CDR3 | NSRDSSYNHWV (SEQ ID NO: 8) |

Therefore, the invention relates to an antibody having specificity for KIT, comprising a heavy chain wherein the variable domain comprises at least one CDR having a sequence selected from the group consisting of SEQ ID NO: 2 for H-CDR1, SEQ ID NO: 3 for H-CDR2 and SEQ ID NO: 4 for H-CDR3.

The invention also relates to an antibody having specificity for KIT, comprising a light chain wherein the variable domain comprises at least one CDR having a sequence selected from the group consisting of SEQ ID NO: 6 for L-CDR1, SEQ ID NO: 7 for L-CDR2 and SEQ ID NO: 8 for L-CDR3.

The antibody of the invention, may comprise a heavy chain wherein the variable domain comprises at least one CDR having a sequence selected from the group consisting of SEQ ID NO: 2 for H-CDR1, SEQ ID NO: 3 for H-CDR2 and SEQ ID NO: 4 for H-CDR3 and a light chain wherein the variable domain comprises at least one CDR having a sequence selected from the group consisting of SEQ ID NO: 6 for L-CDR1, SEQ ID NO: 7 for L-CDR2 and SEQ ID NO: 8 for L-CDR3.

In particular, the invention provides an anti-KIT antibody comprising:

an heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region.

In a particular embodiment, the heavy chain variable region of said antibody has the amino acid sequence set forth as SEQ ID NO: 1 and/or the light chain variable region has the amino acid sequence set forth as SEQ ID NO: 5.

The inventors also have cloned and characterized the variable domain of the light and heavy chains of said scFv 3G1, and thus determined the complementary determining regions (CDRs) domain of said antibody as described in Table 2:

| scFV 3G1 Domains | Sequence |
|---|---|
| VH | MAQVQLVESWGGVAQPGRSLRLSCAAS**GFTFSSFA**MHWVRQAPGKGLEWVAV**TSYDGSNE**YYADSVKGRFTISRDNSKNTLYLQMNSLRAEDTAVYYC**AKAMVRGVTFGDLDY**WGQGTLVTVSS (SEQ ID NO: 9) |
| H-CDR1 | GFTFSSFA (SEQ ID NO: 10) |
| H-CDR2 | TSYDGSNE (SEQ ID NO: 11) |
| H-CDR3 | AKAMVRGVTFGDLDY (SEQ ID NO: 12) |
| VL | SSELTQDPAVSVALGQTVRITCQGD**SLRSYY**ASWYQQKPEQAPVLVIY**GEN**SRPSGIPDRFSGSSSGNTASLTITGAQAEDEADYYC**NSRDSSGTHLRV**FGGGTKLTVLG (SEQ ID NO: 13) |
| L-CDR1 | SLRSYY (SEQ ID NO: 14) |
| L-CDR2 | GEN (SEQ ID NO: 15) |
| L-CDR3 | NSRDSSGTHLRV (SEQ ID NO: 16) |

Therefore, the invention relates to an antibody having specificity for KIT, comprising a heavy chain wherein the variable domain comprises at least one CDR having a sequence selected from the group consisting of SEQ ID NO: 10 for H-CDR1, SEQ ID NO: 11 for H-CDR2 and SEQ ID NO: 12 for H-CDR3.

The invention also relates to an antibody having specificity for KIT, comprising a light chain wherein the variable domain comprises at least one CDR having a sequence selected from the group consisting of SEQ ID NO: 14 for L-CDR1, SEQ ID NO: 15 for L-CDR2 and SEQ ID NO: 16 for L-CDR3.

The antibody of the invention, may comprise a heavy chain wherein the variable domain comprises at least one CDR having a sequence selected from the group consisting of SEQ ID NO: 10 for H-CDR1, SEQ ID NO: 11 for H-CDR2 and SEQ ID NO: 12 for H-CDR3 and a light chain wherein the variable domain comprises at least one CDR having a sequence selected from the group consisting of SEQ ID NO: 14 for L-CDR1, SEQ ID NO: 15 for L-CDR2 and SEQ ID NO: 16 for L-CDR3.

In particular, the invention provides an anti-KIT antibody comprising:

an heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 14 in the L-CDR1 region, SEQ ID NO: 15 in the L-CDR2 region and SEQ ID NO: 16 in the L-CDR3 region.

In a particular embodiment, the heavy chain variable region of said antibody has the amino acid sequence set forth as SEQ ID NO: 9 and/or the light chain variable region has the amino acid sequence set forth as SEQ ID NO: 13

The invention further provides fragments of said antibodies directed against KIT which include but are not limited to Fv, Fab, F(ab')2, Fab', dsFv, scFv, sc(Fv)2 and diabodies.

| ScFV | Sequence |
|---|---|
| 2D1: VH-linker-VL | MAQVKLQESGGGLVQPGGSLRLSCAASGFTFDSYAMSWVRQAPGKGLEWVSYITSSSSTIYYVDSVKGRFTISRDNAKNSLYLQMNSLRDEDTAVYYCARLRNSEGYWYFDLWGRGTLVTVSSGGGGSGGGGSGGGGSQSALTQDPAVSVALGQTVRITCQGDSLRSYFASWYQQKPGQAPLLVMYGQNIRPSGIPDRFSGSSSGNSASLTITGAQAEDEADYYCNSRDSSYNHWVFGGGTKLTVLG (SEQ ID NO: 17) |
| 3G1: VH-linker-VL | MAQVQLVESWGGVAQPGRSLRLSCAASGFTFSSFAMHWVRQAPGKGLEWVAVTSYDGSNEYYADSVKGRFTISRDNSKNTLYLQMNSLRAEDTAVYYCAKAMVRGVTFGDLDYWGQGTLVTVSSGGGGSGGGGSGGGGSSELTQDPAVSVALGQTVRITCQGDSLRSYYASWYQQKPEQAPVLVIYGENSRPSGIPDRFSGSSSGNTASLTITGAQAEDEADYYCNSRDSSGTHLRVFGGGTKLTVLG (SEQ ID NO: 18) |

In one embodiment, said fragment is a scFv having the amino acid sequence set forth as SEQ ID NO: 17.

In another embodiment, said fragment is a scFv having the amino acid sequence set forth as SEQ ID NO: 18

It should be further noted that the antibodies 2D1 and 3G1 cross-react with murin KIT, which is of interest for preclinical evaluation and toxicological studies.

Methods of Producing Antibodies of the Invention:

Anti-KIT antibodies of the invention may be produced by any technique known in the art, such as, without limitation, any chemical, biological, genetic or enzymatic technique, either alone or in combination.

Knowing the amino acid sequence of the desired sequence, one skilled in the art can readily produce said antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques well-known in the art. For example, antibodies can be obtained as DNA expression products after incorporation of DNA sequences encoding the antibodies into expression vectors and introduction of such vectors into suitable eukaryotic or prokaryotic hosts that will express the desired antibodies, from which they can be later isolated using well-known techniques.

Accordingly, a further aspect of the invention relates to a nucleic acid sequence encoding an antibody of the invention. More particularly, the nucleic acid sequence encodes a heavy chain or a light chain of an antibody of the invention as described in Table 3:

| ScFv | Sequence |
|---|---|
| 2D1:VH | ATG GCC CAG GTC AAG CTG CAG GAG TCT GGG GGA GGC TTG GTA CAG CCT GGG GGG TCC CTG AGA CTC TCC TGT GCA GCC TCT GGA TTC ACC TTT GAC AGC TAT GCC ATG AGC TGG GTC CGC CAG GCT CCA GGG AAG GGG CTG GAG TGG GTT TCA TAC ATT ACT AGT AGT AGT AGT ACC ATA TAC TAC GTA GAC TCT GTG AAG GGC CGA TTC ACC ATC TCC AGA GAC AAT GCC AAG AAC TCA CTG TAT CTG CAA ATG AAC AGC CTG AGA GAC GAG GAC ACG GCT GTG TAT TAC TGT GCG AGA CTC CGT AAC TCC GAG GGA TAC TGG TAC TTC GAT CTC TGG GGC CGT GGC ACC CTG GTC ACC GTC TCC TCA (SEQ ID NO: 19) |
| 2D1:VL | TCG CAG TCT GCT CTG ACT CAG GAC CCT GCT GTG TCT GTG GCC TTG GGA CAG ACA GTC AGG ATC ACA TGC CAA GGA GAC AGC CTC AGA AGC TAT TTT GCA AGT TGG TAC CAG CAG AAG CCA GGA CAG GCC CCT CTC CTT GTC ATG TAT GGT CAA AAC ATC CGG CCC TCA GGG ATC CCA GAC CGA TTC TCT GGC TCC AGC TCA GGA AAC TCA GCT TCC TTG ACC ATC ACT GGG GCT CAG GCG GAA GAT GAG GCT GAC TAT TAC TGT AAC TCC CGG GAC AGC AGT TAT AAC CAT TGG GTG TTC GGC GGA GGG ACC AAG CTG ACC GTC CTA GGT (SEQ ID NO: 20) |
| 2D1: VH-<u>linker</u>-VL | ATG GCC CAG GTC AAG CTG CAG GAG TCT GGG GGA GGC TTG GTA CAG CCT GGG GGG TCC CTG AGA CTC TCC TGT GCA GCC TCT GGA TTC ACC TTT GAC AGC TAT GCC ATG AGC TGG GTC CGC CAG GCT CCA GGG AAG GGG CTG GAG TGG GTT TCA TAC ATT ACT AGT AGT AGT AGT ACC ATA TAC TAC GTA GAC TCT GTG AAG GGC CGA TTC ACC ATC TCC AGA GAC AAT GCC AAG AAC TCA CTG TAT CTG CAA ATG AAC AGC CTG AGA GAC GAG GAC ACG GCT GTG TAT TAC TGT GCG AGA CTC CGT AAC TCC GAG GGA TAC TGG TAC TTC GAT CTC TGG GGC CGT GGC ACC CTG GTC ACC GTC TCC TCA <u>GGT GGA GGC GGT TCA GGC GGA GGT GGC TCT GGC GGT GGC GGA</u> TCG CAG TCT GCT CTG ACT CAG GAC CCT GCT GTG TCT GTG GCC TTG GGA CAG ACA GTC AGG ATC ACA TGC CAA GGA GAC AGC CTC AGA AGC TAT TTT GCA AGT TGG TAC CAG CAG AAG CCA GGA CAG GCC CCT CTC CTT GTC ATG TAT GGT CAA AAC ATC CGG CCC TCA GGG ATC CCA GAC CGA TTC TCT GGC TCC AGC TCA GGA AAC TCA GCT TCC TTG ACC ATC ACT GGG GCT CAG GCG GAA GAT GAG GCT GAC TAT TAC TGT AAC TCC CGG GAC AGC AGT TAT AAC CAT TGG GTG TTC GGC GGA GGG ACC AAG CTG ACC GTC CTA GGT (SEQ ID NO: 21) |
| 3G1:VH | ATG GCC CAG GTG CAG CTG GTG GAG TCT TGG GGA GGC GTG GCC CAG CCT GGG AGG TCC CTG AGA CTC TCC TGT GCA GCC TCT GGA TTC ACC TTC AGT AGT TTT GCC ATG CAC TGG GTC CGC CAG GCT CCA GGC AAG GGG CTG GAG TGG GTG GCA GTT ACA TCA TAT GAT GGA AGT AAT GAA TAC TAT GCA GAC TCC GTG AAG GGC CGA TTC ACC ATC TCC AGA GAC AAT TCC AAG AAC ACG CTG TAT CTG CAA ATG AAC AGC CTG AGA GCT GAG GAC ACG GCT GTG TAT TAC TGT GCG AAA GCT ATG GTT CGG GGA GTT ACG TTT GGC GAC CTT GAC TAC TGG GGC CAG GGA ACC CTG GTC ACC GTC TCC TCA (SEQ ID NO: 22) |
| 3G1:VL | TCG TCT GAG CTG ACT CAG GAC CCT GCT GTG TCT GTG GCC TTG GGA CAG ACA GTC AGA ATC ACA TGC CAA GGA GAC AGC CTC AGA AGT TAT TAT GCA AGC TGG TAC CAG CAG AAG CCA GAA CAG GCC CCT GTA CTT GTC ATC TAT GGT GAA AAC AGC CGG CCC TCA GGG ATC CCA GAC CGA TTC TCT GGC TCC AGC TCA GGA AAC ACA GCT TCC TTG ACC ATC ACT GGG GCT CAG GCG GAA GAT GAG GCT GAC TAT TAC TGC AAC TCT CGC GAC AGC AGT GGT ACC CAT CTA AGG GTA TTC GGC GGA GGG ACC AAG CTG ACC GTC CTA GGT (SEQ ID NO: 23) |
| 3G1: VH-<u>linker</u>-VL | ATG GCC CAG GTG CAG CTG GTG GAG TCT TGG GGA GGC GTG GCC CAG CCT GGG AGG TCC CTG AGA CTC TCC TGT GCA GCC TCT GGA TTC ACC TTC AGT AGT TTT GCC ATG CAC TGG GTC CGC CAG GCT CCA GGC AAG GGG CTG GAG TGG GTG GCA GTT ACA TCA TAT GAT GGA AGT AAT GAA TAC TAT GCA GAC TCC GTG AAG GGC CGA TTC ACC ATC TCC AGA GAC AAT TCC AAG AAC ACG CTG TAT CTG CAA ATG AAC AGC CTG AGA GCT GAG GAC ACG GCT GTG TAT TAC TGT GCG AAA GCT ATG GTT CGG GGA GTT ACG TTT GGC GAC CTT GAC TAC TGG GGC CAG GGA ACC CTG GTC ACC GTC TCC TCA <u>GGT GGA GGC GGT TCA GGC GGA GGT GGC TCT GGC GGT GGC GGA</u> TCG TCT GAG CTG ACT CAG GAC CCT GCT GTG TCT GTG GCC TTG GGA CAG ACA GTC AGA ATC ACA TGC CAA GGA GAC AGC CTC AGA AGT TAT TAT GCA AGC TGG TAC CAG CAG AAG CCA GAA CAG GCC CCT GTA CTT GTC ATC TAT GGT GAA AAC AGC CGG CCC TCA GGG ATC CCA GAC CGA TTC TCT GGC TCC AGC TCA GGA AAC ACA GCT TCC TTG ACC ATC ACT GGG GCT CAG GCG GAA GAT GAG GCT GAC TAT TAC TGC AAC TCT CGC GAC AGC AGT GGT ACC CAT CTA AGG GTA TTC GGC GGA GGG ACC AAG CTG ACC GTC CTA GGT (SEQ ID NO: 24) |

Typically, said nucleic acid is a DNA or RNA molecule, which may be included in any suitable vector, such as a plasmid, cosmid, episome, artificial chromosome, phage or a viral vector.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said antibody upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a host cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce an antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene ("DHFR gene") is defective (Urlaub G et al; 1980), rat YB2/3HL.P2.G11.16Ag.20 cell (ATCC CRL1662, hereinafter referred to as "YB2/0 cell"), and the like.

The invention also relates to a method of producing a recombinant host cell expressing an antibody according to the invention, said method comprising the steps of: (i) introducing in vitro or ex vivo a recombinant nucleic acid or a vector as described above into a competent host cell, (ii) culturing in vitro or ex vivo the recombinant host cell obtained and (iii), optionally, selecting the cells which express and/or secrete said antibody. Such recombinant host cells can be used for the production of antibodies of the invention.

Antibodies of the invention are suitably separated from the culture medium by conventional immunoglobulin purification procedures such as protein A-Sepharose, hydroxylapatite chromatography, gel electrophoresis, dialysis, or affinity chromatography.

Amino acid sequence modification(s) of the antibodies described herein are contemplated. For example, it may be desirable to improve the binding affinity and/or other biological properties of the antibody. Modifications and changes may be made in the structure of the antibodies of the invention, and in the DNA sequences encoding them, and still obtain a functional molecule that encodes an antibody with desirable characteristics.

In making the changes in the amino sequences, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

A further aspect of the invention also encompasses function-conservative variants of the antibodies of the invention.

"Function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like). Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared.

Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical) over the whole length of the shorter sequence. Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted by other amino acids in a protein structure without appreciable loss of activity. Since the interactive capacity and nature of a protein define the protein's biological functional activity, certain amino acid substitutions can be made in a protein sequence, and, of course, in its DNA encoding sequence, while nevertheless obtaining a protein with like properties. It is thus contemplated that various changes may be made in the antibodies sequences of the invention, or corresponding DNA sequences which encode said antibodies, without appreciable loss of their biological activity.

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

Accordingly, the invention also provides an antibody comprising a heavy chain wherein the variable domain comprises:

- a H-CDR1 having at least 90% or 95% identity with sequence set forth as SEQ ID NO: 2,
- a H-CDR2 having at least 90% or 95% identity with sequence set forth as SEQ ID NO: 3,
- a H-CDR3 having at least 90% or 95% identity with sequence set forth as SEQ ID NO: 4,
- a L-CDR1 having at least 90% or 95% identity with sequence set forth as SEQ ID NO: 6,
- a L-CDR2 having at least 90% or 95% identity with sequence set forth as SEQ ID NO: 7,
- a L-CDR3 having at least 90% or 95% identity with sequence set forth as SEQ ID NO: 8, and
- that specifically binds to KIT with substantially the same affinity as an antibody comprising a heavy chain wherein the variable domain comprises SEQ ID NO: 2 for H-CDR1, SEQ ID NO: 3 for H-CDR2 and SEQ ID NO: 4 for H-CDR3 and a light chain wherein the variable domain comprises SEQ ID NO: 6 for L-CDR1, SEQ ID NO: 7 for L-CDR2 and SEQ ID NO: 8 for L-CDR3, and more preferably with substantially the same affinity as the the bivalent scFv-Fc 2D1.

The inventors have cloned and characterized the variable domain of the light chains of a variant of 2D1 displaying an increased affinity, referred as 2D1-C7, and thus determined the complementary determining regions (CDRs) domain of said antibody as described in Table 4:

| 2D1-C7 Domains | Sequence |
|---|---|
| VH | MAQVKLQESGGGLVQPGGSLRLSCAASGFTFDSYAMSWVRQAPGKGLEWVSYITSSSSTIYYVDSVKGRFTISRDNAKNSLYLQMNSLRDEDTAVYYCARLRNSEGYWYFDLWGRGTLVTVSS (SEQ ID NO: 1) |
| H-CDR1 | GFTFDSYA (SEQ ID NO: 2) |
| H-CDR2 | ITSSSSTI (SEQ ID NO: 3) |
| H-CDR3 | RLRNSEGYWYFDL (SEQ ID NO: 4) |
| VL | SQS**V**LTQDPAVSVALGQTVRITCQGD**SLRSYY**ASWYQQKPGQAPLLVMY**GEN**IRPSGIPDRFSGS**T**SGNSASLTITGAQAEDEADYYC**NSRDSSGNHLNWV**FGGGTKLTVLG (SEQ ID NO: 26) |
| L-CDR1 | SLRSYY (SEQ ID NO: 27) |
| L-CDR2 | GEN (SEQ ID NO: 28) |
| L-CDR3 | NSRDSSGNHLNWV (SEQ ID NO: 29) |

Therefore, the invention relates to an antibody having specificity for KIT, comprising a heavy chain wherein the variable domain comprises at least one CDR having a sequence selected from the group consisting of SEQ ID NO: 2 for H-CDR1, SEQ ID NO: 3 for H-CDR2 and SEQ ID NO: 4 for H-CDR3.

The invention also relates to an antibody having specificity for KIT, comprising a light chain wherein the variable domain comprises at least one CDR having a sequence selected from the group consisting of SEQ ID NO: 27 for L-CDR1, SEQ ID NO: 28 for L-CDR2 and SEQ ID NO: 29 for L-CDR3.

The antibody of the invention, may comprise a heavy chain wherein the variable domain comprises at least one CDR having a sequence selected from the group consisting of SEQ ID NO: 2 for H-CDR1, SEQ ID NO: 3 for H-CDR2 and SEQ ID NO: 4 for H-CDR3 and a light chain wherein the variable domain comprises at least one CDR having a sequence selected from the group consisting of SEQ ID NO: 27 for L-CDR1, SEQ ID NO: 28 for L-CDR2 and SEQ ID NO: 29 for L-CDR3.

In particular, the invention provides an anti-KIT antibody comprising:

- an heavy chain variable region comprising SEQ ID NO: 2 in the H-CDR1 region, SEQ ID NO: 3 in the H-CDR2 region and SEQ ID NO: 4 in the H-CDR3 region; and
- a light chain variable region comprising SEQ ID NO: 27 in the L-CDR1 region, SEQ ID NO: 28 in the L-CDR2 region and SEQ ID NO: 29 in the L-CDR3 region.

In a particular embodiment, the heavy chain variable region of said antibody has the amino acid sequence set forth as SEQ ID NO: 1 and/or the light chain variable region has the amino acid sequence set forth as SEQ ID NO: 26

The invention further provides an antibody comprising a heavy chain wherein the variable domain comprises:

- a H-CDR1 having at least 90% or 95% identity with sequence set forth as SEQ ID NO: 10,
- a H-CDR2 having at least 90% or 95% identity with sequence set forth as SEQ ID NO: 11,
- a H-CDR3 having at least 90% or 95% identity with sequence set forth as SEQ ID NO: 12, a L-CDR1 having at least 90% or 95% identity with sequence set forth as SEQ ID NO: 14, a L-CDR2 having at least 90% or 95% identity with sequence set forth as SEQ ID NO: 15, a L-CDR3 having at least 90% or 95% identity with sequence set forth as SEQ ID NO: 16, and that specifically binds to KIT with substantially the same affinity as an antibody comprising a heavy chain wherein the variable domain comprises SEQ ID NO: 10 for H-CDR1, SEQ ID NO: 11 for H-CDR2 and SEQ ID NO: 12 for H-CDR3 and a light chain wherein the variable domain comprises SEQ ID NO: 14 for L-CDR1, SEQ ID NO: 15 for L-CDR2 and SEQ ID NO: 16 for L-CDR3, and more preferably with substantially the same affinity as the bivalent scFv-Fc 3G1.

The inventors have cloned and characterized the variable domain of the light chains of a variant of 3G1 displaying an increased affinity, referred as 3G1-A2, and thus determined the complementary determining regions (CDRs) domain of said antibody as described in Table 5:

| 3G1-A2 Domains | Sequence |
|---|---|
| VH | MAQVQLVESWGGVAQPGRSLRLSCAAS**GFTFSSFA**MHW VRQAPGKGLEWVAV**TSYDGSNE**YYADSVKGRFTISRDN SKNTLYLQMNSLRAEDTAVYYC**AKAMVRGVTFGDLDY**W GQGTLVTVSS (SEQ ID NO: 9) |
| H-CDR1 | GFTFSSFA (SEQ ID NO: 10) |
| H-CDR2 | TSYDGSNE (SEQ ID NO: 11) |
| H-CDR3 | AKAMVRGVTFGDLDY (SEQ ID NO: 12) |
| VL | SSELTQDPAVSVALGQTVR**K**TCQGD**SLKSYY**ASWYQQK P**G**QAPVLVIY**GEN**SRPSGIPDRFSGSSSGNTASLTITG AQAEDEADYYC**CSRATGGYHRI**FGGGTKLTVLG (SEQ ID NO: 30) |
| L-CDR1 | SLKSYY (SEQ ID NO:31) |
| L-CDR2 | GEN (SEQ ID NO: 32) |
| L-CDR3 | CSRATGGYHRI (SEQ ID NO: 33) |

Therefore, the invention relates to an antibody having specificity for KIT, comprising a heavy chain wherein the variable domain comprises at least one CDR having a sequence selected from the group consisting of SEQ ID NO: 10 for H-CDR1, SEQ ID NO: 11 for H-CDR2 and SEQ ID NO: 12 for H-CDR3.

The invention also relates to an antibody having specificity for KIT, comprising a light chain wherein the variable domain comprises at least one CDR having a sequence selected from the group consisting of SEQ ID NO: 31 for L-CDR1, SEQ ID NO: 32 for L-CDR2 and SEQ ID NO: 33 for L-CDR3.

The antibody of the invention, may comprise a heavy chain wherein the variable domain comprises at least one CDR having a sequence selected from the group consisting of SEQ ID NO: 10 for H-CDR1, SEQ ID NO: 11 for H-CDR2 and SEQ ID NO: 12 for H-CDR3 and a light chain wherein the variable domain comprises at least one CDR having a sequence selected from the group consisting of SEQ ID NO: 31 for L-CDR1, SEQ ID NO: 32 for L-CDR2 and SEQ ID NO: 33 for L-CDR3.

In particular, the invention provides an anti-KIT antibody comprising:

an heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 31 in the L-CDR1 region, SEQ ID NO: 32 in the L-CDR2 region and SEQ ID NO: 33 in the L-CDR3 region.

In a particular embodiment, the heavy chain variable region of said antibody has the amino acid sequence set forth as SEQ ID NO: 9 and/or the light chain variable region has the amino acid sequence set forth as SEQ ID NO: 30.

Said antibodies may be assayed for specific binding by any method known in the art. Many different competitive binding assay format(s) can be used for epitope binning. The immunoassays which can be used include, but are not limited to, competitive assay systems using techniques such western blots, radioimmunoassays, ELISA, "sandwich" immunoassays, immunoprecipitation assays, precipitin assays, gel diffusion precipitin assays, immunoradiometric assays, fluorescent immunoassays, protein A immunoassays, and complement-fixation assays. Such assays are routine and well known in the art (see, e.g., Ausubel et al., eds, 1994 Current Protocols in Molecular Biology, Vol. 1, John Wiley & sons, Inc., New York). For example, the BIACORE® (GE Healthcare, Piscataway, N.J.) is one of a variety of surface plasmon resonance assay formats that are routinely used to epitope bin panels of monoclonal antibodies. Additionally, routine cross-blocking assays such as those described in Antibodies, A Laboratory Manual, Cold Spring Harbor Laboratory, Ed Harlow and David Lane, 1988, can be performed.

Engineered antibodies of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention. Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 by Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc receptor by modifying one or more amino acids. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al., 2001 J. Biol. Chen. 276:6591-6604, WO2010106180).

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated or non-fucosylated antibody having reduced amounts of or no fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation or are devoid of fucosyl residues. Therefore, in one embodiment, the antibodies of the invention may be produced by recombinant expression in a cell line which exhibit hypofucosylation or non-fucosylation pattern, for example, a mammalian cell line with deficient expression of the FUT8 gene encoding fucosyltransferase. PCT Publication WO 03/035835 by Presta describes a variant CHO cell line, Lecl3 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Eureka Therapeutics further describes genetically engineered CHO mammalian cells capable of producing antibodies with altered mammalian glycosylation pattern devoid of fucosyl residues.

Alternatively, the antibodies of the invention can be produced in yeasts or filamentous fungi engineered for mammalian-like glycosylation pattern and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP0154316 by Nishimura et al. and EP0401384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094. Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Immunoconjugates:

An antibody of the invention can be conjugated with a detectable label to form an anti-KIT immunoconjugate. Suitable detectable labels include, for example, a radioisotope, a fluorescent label, a chemiluminescent label, an enzyme label, a bioluminescent label or colloidal gold. Methods of making and detecting such detectably-labeled immunoconjugates are well-known to those of ordinary skill in the art, and are described in more detail below.

The detectable label can be a radioisotope that is detected by autoradiography. Isotopes that are particularly useful for the purpose of the present invention are $^{3}H$, $^{125}I$, $^{131}I$, $^{35}S$ and $^{14}C$.

Anti-KIT immunoconjugates can also be labeled with a fluorescent compound. The presence of a fluorescently-labeled antibody is determined by exposing the immunoconjugate to light of the proper wavelength and detecting the resultant fluorescence. Fluorescent labeling compounds include fluorescein isothiocyanate, rhodamine, phycoerytherin, phycocyanin, allophycocyanin, o-phthaldehyde and fluorescamine.

Alternatively, anti-KIT immunoconjugates can be detectably labeled by coupling an antibody to a chemiluminescent compound. The presence of the chemiluminescent-tagged immunoconjugate is determined by detecting the presence of luminescence that arises during the course of a chemical reaction. Examples of chemiluminescent labeling compounds include luminol, isoluminol, an aromatic acridinium ester, an imidazole, an acridinium salt and an oxalate ester.

Similarly, a bioluminescent compound can be used to label anti-KIT immunoconjugates of the present invention. Bioluminescence is a type of chemiluminescence found in biological systems in which a catalytic protein increases the efficiency of the chemiluminescent reaction. The presence of a bioluminescent protein is determined by detecting the presence of luminescence. Bioluminescent compounds that are useful for labeling include luciferin, luciferase and aequorin.

Alternatively, anti-KIT immunoconjugates can be detectably labeled by linking an anti-KIT antibody to an enzyme. When the anti-KIT-enzyme conjugate is incubated in the presence of the appropriate substrate, the enzyme moiety reacts with the substrate to produce a chemical moiety which can be detected, for example, by spectrophotometric, fluorometric or visual means. Examples of enzymes that can be used to detectably label polyspecific immunoconjugates include β-galactosidase, glucose oxidase, peroxidase and alkaline phosphatase.

Those of skill in the art will know of other suitable labels which can be employed in accordance with the present invention. The binding of marker moieties to anti-KIT monoclonal antibodies can be accomplished using standard techniques known to the art. Typical methodology in this regard is described by Kennedy et al., *Clin. Chim. Acta* 70:1, 1976; Schurs et al., *Clin. Chim. Acta* 81:1, 1977; Shih et al., *Int'l J. Cancer* 46:1101, 1990; Stein et al., *Cancer Res.* 50:1330, 1990; and Coligan, supra.

Moreover, the convenience and versatility of immunochemical detection can be enhanced by using anti-KIT monoclonal antibodies that have been conjugated with avidin, streptavidin, and biotin. (See, e.g., Wilchek et al. (eds.), “Avidin-Biotin Technology,” *Methods In Enzymology* (Vol. 184) (Academic Press 1990); Bayer et al., “Immunochemical Applications of Avidin-Biotin Technology,” in *Methods In Molecular Biology* (Vol. 10) 149-162 (Manson, ed., The Humana Press, Inc. 1992).)

Methods for performing immunoassays are well-established. (See, e.g., Cook and Self, “Monoclonal Antibodies in Diagnostic Immunoassays,” in *Monoclonal Antibodies: Production, Engineering, and Clinical Application* 180-208 (Ritter and Ladyman, eds., Cambridge University Press 1995); Perry, “The Role of Monoclonal Antibodies in the Advancement of Immunoassay Technology,” in *Monoclonal Antibodies: Principles and Applications* 107-120 (Birch and Lennox, eds., Wiley-Liss, Inc. 1995); Diamandis, *Immunoassay* (Academic Press, Inc. 1996).)

In another aspect, the invention provides an anti-KIT antibody-drug conjugate. An “anti-KIT antibody-drug conjugate” as used herein refers to an anti-KIT antibody according to the invention conjugated to a therapeutic agent. Such anti-KIT antibody-drug conjugates produce clinically beneficial effects on KIT-expressing cells when administered to a patient, such as, for example, a patient with a KIT-expressing cancer, typically when administered alone but also in combination with other therapeutic agents.

In typical embodiments, an anti-KIT antibody is conjugated to a cytotoxic agent, such that the resulting antibody-drug conjugate exerts a cytotoxic or cytostatic effect on a KIT-expressing cell (e.g., a KIT-expressing cancer cell) when taken up or internalized by the cell. Particularly suitable moieties for conjugation to antibodies are chemotherapeutic agents, prodrug converting enzymes, radioactive isotopes or compounds, or toxins. For example, an anti-KIT antibody can be conjugated to a cytotoxic agent such as a chemotherapeutic agent or a toxin (e.g., a cytostatic or cytocidal agent such as, for example, abrin, ricin A, pseudomonas exotoxin, or diphtheria toxin).

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and-carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, or the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065 (Li et al., *Cancer Res.* 42:999-1004, 1982), chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, etopside phosphate (VP-16), 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide (VM-26), 6-thioguanine, thioTEPA, topotecan, vinblastine, vincristine, and vinorelbine.

Particularly suitable cytotoxic agents include, for example, dolastatins (e.g., auristatin E, AFP, MMAF, MMAE), DNA minor groove binders (e.g., enediynes and lexitropsins), duocarmycins, taxanes (e.g., paclitaxel and docetaxel), puromycins, vinca alkaloids, CC-1065, SN-38 (7-ethyl-10-hydroxy-camptothein), topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discodermolide, eleutherobin, and mitoxantrone. In certain embodiments, a cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be linked to an anti-KIT antibody.

In specific variations, the cytotoxic or cytostatic agent is auristatin E (also known in the art as dolastatin-10) or a derivative thereof. Typically, the auristatin E derivative is, e.g., an ester formed between auristatin E and a keto acid. For example, auristatin E can be reacted with paraacetyl benzoic acid or benzoylvaleric acid to produce AEB and AEVB, respectively. Other typical auristatin derivatives include AFP (dimethylvaline-valine-dolaisoleuine-dolaproine-phenylalanine-p-phenylenediamine), MMAF (dovaline-valine-dolaiso leunine-dolaproine-phenylalanine), and MAE (monomethyl auristatin E). The synthesis and structure of auristatin E and its derivatives are described in U.S. Patent Application Publication No. 20030083263; International Patent Publication Nos. WO 2002/088172 and WO 2004/010957; and U.S. Pat. Nos. 6,884,869; 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In other variations, the cytotoxic agent is a DNA minor groove binding agent. (See, e.g., U.S. Pat. No. 6,130,237.) For example, in certain embodiments, the minor groove binding agent is a CBI compound. In other embodiments, the minor groove binding agent is an enediyne (e.g., calicheamicin).

In certain embodiments, an antibody-drug conjugate comprises an anti-tubulin agent. Examples of anti-tubulin agents include, for example, taxanes (e.g., Taxol® (paclitaxel), Taxotere® (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin. In some embodiments, the cytotoxic agent is a maytansinoid, another group of anti-tubulin agents. For example, in specific embodiments, the maytansinoid is maytansine or DM-1 (ImmunoGen, Inc.; see also Chari et al., *Cancer Res.* 52:127-131, 1992).

In other embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, an anti-KIT antibody is conjugated to a pro-drug converting enzyme. The pro-drug converting enzyme can be recombinantly fused to the antibody or chemically conjugated thereto using known methods. Exemplary pro-drug converting enzymes are carboxypeptidase G2, β-glucuronidase, penicillin-V-amidase, penicillin-G-amidase, β-lactamase, β-glucosidase, nitroreductase and carboxypeptidase A.

Techniques for conjugating therapeutic agents to proteins, and in particular to antibodies, are well-known. (See, e.g., Amon et al., "Monoclonal Antibodies For Immunotargeting Of Drugs In Cancer Therapy," in *Monoclonal Antibodies And Cancer Therapy* (Reisfeld et al. eds., Alan R. Liss, Inc., 1985); Hellstrom et al., "Antibodies For Drug Delivery," in *Controlled Drug Delivery* (Robinson et al. eds., Marcel Deiker, Inc., 2nd ed. 1987); Thorpe, "Antibody Carriers Of Cytotoxic Agents In Cancer Therapy: A Review," in *Monoclonal Antibodies '84: Biological And Clinical Applications* (Pinchera et al. eds., 1985); "Analysis, Results, and Future Prospective of the Therapeutic Use of Radiolabeled Antibody In Cancer Therapy," in *Monoclonal Antibodies For Cancer Detection And Therapy* (Baldwin et al. eds., Academic Press, 1985); and Thorpe et al., 1982, *Immunol. Rev.* 62:119-58. See also, e.g., PCT publication WO 89/12624.)

Diagnostic Uses:

A further aspect of the invention relates to an anti-KIT antibody of the invention for diagnosing and/or monitoring a cancer disease and other diseases in which KIT levels are modified (increase or decrease).

In a preferred embodiment, antibodies of the invention may be labelled with a detectable molecule or substance, such as a fluorescent molecule, a radioactive molecule or any others labels known in the art as above described. For example, an antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, mri), such as iodine-123, iodine-131, indium-Ill, fluorine-19, carbon-13, nitrogen-15, oxygen-17, gadolinium, manganese or iron. Following administration of the antibody, the distribution of the antibody within the patient is detected. Methods for detecting distribution of any specific label are known to those skilled in the art and any appropriate method can be used. Some non-limiting examples include, computed tomography (CT), position emission tomography (PET), magnetic resonance imaging (MRI), fluorescence, chemiluminescence and sonography.

Antibodies of the invention may be useful for diagnosing and staging of cancer diseases associated with KIT overexpression (e.g., in radioimaging). Cancer diseases associated with KIT overexpression typically include but are not limited to gastrointestinal stromal cancer (GIST), hematological cancers (e.g. leukemias such as acute myeloid leukemia (AML)), small-cell lung cancer, pancreatic cancer, mastocytoma, ovarian cancer, breast cancer, melanoma, colon cancer, colorectal cancer, testicular semimoma, other KIT expressing or overexpressing hyperproliferative diseases.

Antibodies of the invention may be useful for diagnosing diseases other than cancers for which KIT expression is increased or decreased (soluble or cellular KIT form).

Typically, said diagnostic methods involve use of biological sample obtained from the patient. As used herein the term "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease associated with KIT overexpression, and in a preferred embodiment from GIST, AML, small-cell lung cancer, pancreatic cancer, mastocytoma, ovarian cancer, breast cancer, melanoma. Therefore, biological samples encompass clinical samples, cells in culture, cell supernatants, cell lysates, serum, plasma, biological fluid, and tissue samples.

In a particular embodiment, the invention is a method of diagnosing a cancer disease associated with KIT overexpression in a subject by detecting KIT on cells from the subject using the antibody of the invention. In particular, said method of diagnosing may comprise the steps consisting of:

(a) contacting a biological sample of a subject likely to suffer from a cancer disease associated with KIT overexpression with an antibody according to the invention in conditions sufficient for the antibody to form complexes with cells of the biological sample that express KIT;

(b) detecting and/or quantifying said complexes, whereby the detection of said complexes is indicative of a cancer disease associated with KIT overexpression.

In order to monitor the cancer disease, the method of diagnosing according to the invention may be repeated at different intervals of time, in order to determine if antibody binding to the samples increases or decreases, whereby it is determined if the cancer disease progresses or regresses.

Therapeutic Uses:

Antibodies, fragments or immunoconjugates of the invention may be useful for treating any disease associated with KIT expression preferentially cancers. The antibodies of the invention may be used alone or in combination with any suitable agent.

An anti-KIT antibody of the invention may be used as treatment of hyperproliferative diseases associated with KIT expression, overexpression and/or activation.

Examples of such diseases associated with KIT expression, overexpression or activation encompasses to gastrointestinal stromal cancer (GIST), hematological cancers (e.g. leukemias such as acute myeloid leukemia (AML)), small-cell lung cancer, pancreatic cancer, mastocytoma, ovarian cancer, breast cancer, melanoma, colon cancer, colorectal cancer, testicular semimoma, other KIT expressing or overexpressing hyperproliferative diseases. More preferable cancers are GIST, AML, small-cell lung cancer, pancreatic cancer, mastocytoma, ovarian cancer, breast cancer and melanoma.

As previously mentioned, two groups of activating mutations exist in cancer associated with KIT overexpression or activation: regulation type mutations such as KIT V560G in GIST and enzymatic type mutations such as KIT D816V in acute myeloid lymphoma (AML).

In one particular embodiment, said hyperproliferative diseases associated with KIT expression, overexpression and/or activation are TKI-resistant diseases such as for instance imatinib-resistant GIST or AML. Such diseases may display primary resistance with catalytic mutants of KIT (mutations in activation loop) or secondary resistance with mutations in drug binding residues (gatekeeper mutations such as T670I or V654A).

In each of the embodiments of the treatment methods described herein, the anti-KIT antibody or anti-KIT antibody-drug conjugate is delivered in a manner consistent with conventional methodologies associated with management of the disease or disorder for which treatment is sought. In accordance with the disclosure herein, an effective amount of the antibody or antibody-drug conjugate is administered to a patient in need of such treatment for a time and under conditions sufficient to prevent or treat the disease or disorder.

Thus, an aspect of the invention relates to a method for treating a disease associated with the overexpression and/or the activation of KIT comprising administering a patient in need thereof with a therapeutically effective amount of an antibody, fragment or immunoconjugate of the invention.

In the context of the invention, the term "treating" or "treatment", as used herein, means reversing, alleviating, inhibiting the progress of, or preventing the disorder or condition to which such term applies, or one or more symptoms of such disorder or condition.

According to the invention, the term "patient" or "patient in need thereof" is intended for a human affected or likely to be affected with disease associated with the overexpression and/or the activation of KIT.

By a "therapeutically effective amount" of the antibody of the invention is meant a sufficient amount of the antibody to treat said disease associated with the overexpression and/or the activation of KIT such as a cancer (e.g. GIST or CML), at a reasonable benefit/risk ratio applicable to any medical treatment. It will be understood, however, that the total daily usage of the antibodies and compositions of the present invention will be decided by the attending physician within the scope of sound medical judgment. The specific therapeutically effective dose level for any particular patient will depend upon a variety of factors including the disorder being treated and the severity of the disorder; activity of the specific antibody employed; the specific composition employed, the age, body weight, general health, sex and diet of the patient; the time of administration, route of administration, and rate of excretion of the specific antibody employed; the duration of the treatment; drugs used in combination or coincidental with the specific antibody employed; and like factors well known in the medical arts. For example, it is well known within the skill of the art to start doses of the compound at levels lower than those required to achieve the desired therapeutic effect and to gradually increase the dosage until the desired effect is achieved.

In certain embodiments, an anti-KIT antibody or antibody-drug conjugate is used in combination with a second agent for treatment of a disease or disorder. When used for treating cancer, an anti-KIT antibody or antibody-drug conjugate of the invention may be used in combination with conventional cancer therapies such as, e.g., surgery, radiotherapy, chemotherapy, or combinations thereof.

In certain aspects, other therapeutic agents useful for combination cancer therapy with an anti-KIT antibody or antibody-drug conjugate in accordance with the invention include anti-angiogenic agents. In some aspects, an antibody or antibody-drug conjugate in accordance with the invention is co-administered with a cytokine (e.g., a cytokine that stimulates an immune response against a tumor).

In some embodiments, an anti-KIT monoclonal antibody or antibody-drug conjugate as described herein is used in combination with a tyrosine kinase inhibitor (TKI).

In one embodiment, the TKI is selected from the group consisting of N-phenyl-2-pyrimidine-amine derivatives as described in EP0564409, pyrimidinylaminobenzamide derivatives as described in WO2004005281, cyclic compounds as described in WO0062778, bicyclic heteroaryl compounds as described in WO 2007075869, substituted 3-cyano quinoline derivatives as described in U.S. Pat. No. 6,002,008, 4-anilo-3-quinolinecarbonitrile derivatives as described in WO200504669 and amide derivatives as described in U.S. Pat. No. 7,728,131 and WO2005063709.

In a particular embodiment, the TKI is selected from the group consisting of imatinib, nilotinib, dasatinib, ponatinib, bosutinib and bafetinib.

In a preferred embodiment, the TKI is imatinib or 4-[(4-methylpiperazin-1-yl)methyl]-N-(4-methyl-3-{[4-(pyridin-3-yl)pyrimidin-2-yl]amino}phenyl)benzamide (marketed as GLIVEC® by Novartis and previously known as STI571) of formula (I):

(I)

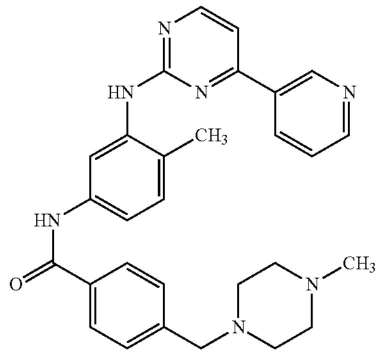

In a preferred embodiment, the TKI is nilotinib or 4-methyl-N-[3-(4-methyl-1H-imidazol-1-yl)-5-(trifluoromethyl)phenyl]-3-[(4-pyridin-3-ylpyrimidin-2-yl)amino]benzamide (marketed as TASIGNA® by Novartis and previously known as AMN107) of formula (II):

(II)

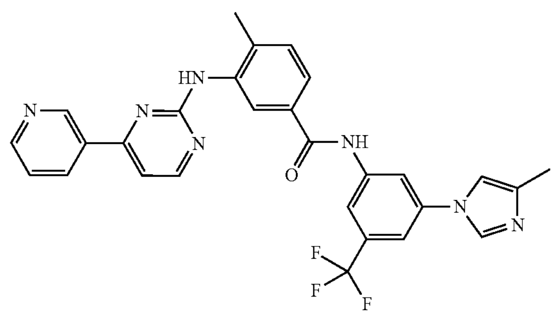

In a preferred embodiment, the TKI is dasatinib or N-(2-chloro-6-methylphenyl)-2-[[6-[4-(2-hydroxyethyl)-1-piperazinyl]-2-methyl-4-pyrimidinyl]amino]-5-thiazole-carboxamide monohydrate (marketed as SPRYCEL® by BMS and previously known as BMS-354825) of formula (III):

(III)

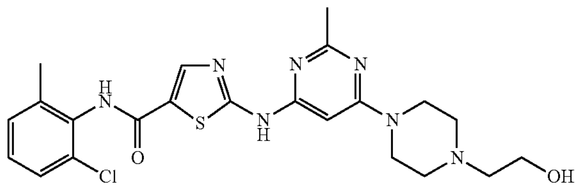

In a preferred embodiment, the TKI is ponatinib or 3-(2-imidazo[1,2-b]pyridazin-3-ylethynyl)-4-methyl-N-[4-[(4-methylpiperazin-1-yl)methyl]-3-(trifluoromethyl)phenyl]benzamide (marketed as ICLUSIG® by and previously known as AP24534) of formula (IV):

(IV)

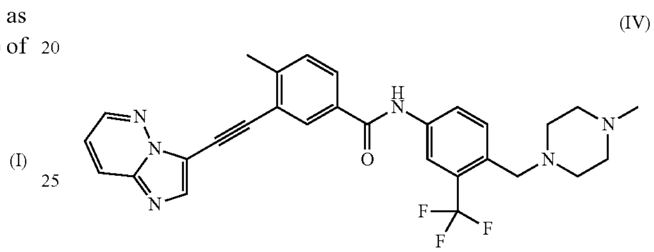

In a preferred embodiment, the TKI is bosutinib or 4-[(2,4-dichloro-5-methoxyphenyl)amino]-6-methoxy-7-[3-(4-methylpiperazin-1-yl)propoxy]quinoline-3-carbonitrile (marketed as BOSULIF® by PFIZER and previously known as SKI-606) of formula (V):

(V)

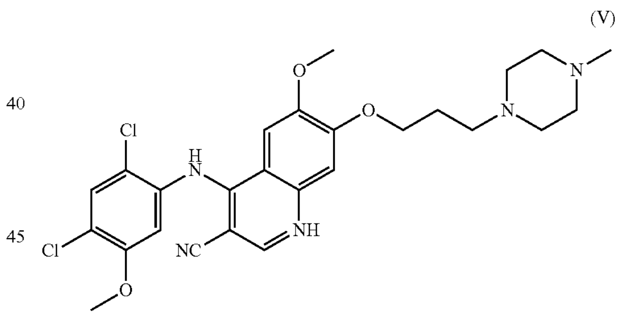

In some embodiments, an anti-KIT antibody or antibody-drug conjugate as described herein is used in combination with a therapeutic monoclonal antibody (mAb). Trastuzumab (Herceptin, Roche), Bevacizumab (Avastin, Roche) and Cetuximab (Erbitux, Merck) are three such mAb that have been approved. Other mAb include, but are not limited to: Infliximab (Remicade, Johnson&Johnson), Rituximab (Rituxan, Roche), Adalimumab (Humira, Abbott) and Natalizumab (Tysabri, Biogen).

Pharmaceutical Compositions:

For administration, the anti-KIT antibody or antibody-drug conjugate is formulated as a pharmaceutical composition. A pharmaceutical composition comprising an anti-KIT antibody or antibody-drug conjugate can be formulated according to known methods to prepare pharmaceutically useful compositions, whereby the therapeutic molecule is combined in a mixture with a pharmaceutically acceptable carrier. A composition is said to be a "pharmaceutically acceptable carrier" if its administration can be tolerated by a recipient patient. Sterile phosphate-buffered saline is one example of a pharmaceutically acceptable carrier. Other suitable carriers are well-known to those in the art. (See, e.g., Gennaro (ed.), Remington's Pharmaceutical Sciences (Mack Publishing Company, 19th ed. 1995)) Formulations may further include one or more excipients, preservatives, solubilizers, buffering agents, albumin to prevent protein loss on vial surfaces, etc.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antibody may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antibody of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antibodies of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antibodies into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be are easily made.

Liposomes are formed from phospho lipids that are dispersed in an aqueous medium and spontaneously form multilamellar concentric bilayer vesicles (also termed multilamellar vesicles (MLVs)). MLVs generally have diameters of from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

Kits:

Finally, the invention also provides kits comprising at least one antibody of the invention. Kits containing antibodies of the invention find use in detecting KIT expression (increase or decrease), or in therapeutic or diagnostic assays. Kits of the invention can contain an antibody coupled to a solid support, e.g., a tissue culture plate or beads (e.g., sepharose beads). Kits can be provided which contain antibodies for detection and quantification of KIT in vitro, e.g. in an ELISA or a Western blot. Such antibody useful for detection may be provided with a label such as a fluorescent or radiolabel.

The invention will be further illustrated by the following figures and examples. However, these examples and figures should not be interpreted in any way as limiting the scope of the present invention.

FIGURES

FIG. 1: Selection and initial characterization of a panel of anti-KIT scFvs. (A) SDS-PAGE analysis of KIT-ECD produced in High Five cells infected by a recombinant baculovirus and purified after Ni-NTA affinity chromatography. (B) Western blot analysis of purified KIT-ECD with an anti-KIT N-terminal monoclonal antibody (Santa Cruz). (C) Analysis of the phage antibody diversity obtained in the $2^{nd}$ and $3^{rd}$ rounds of selection. Clones of phage antibody that were positive on ELISA for binding to KIT-ECD were sequenced. (D) FACS analysis of scFv binding to HMC1.2 cells. ScFvs were induced with IPTG 1 mM overnight at 25° C. from TG1 bacterial containing pHEN phagemid. Supernatant was collected, concentrated on Amicon ultra-4 centrifugal units and incubated with HMC1.2 cells at 4° C. ScFv binding to cells was detected with an anti-c-myc antibody and anti-mouse immunoglobulins conjugated to phycoerythrin. Fluorescence was measured by FACS. MFI signal greater than 9 (MFI obtained with non specific Bot-Fc) was considered positive.

Figure 2:
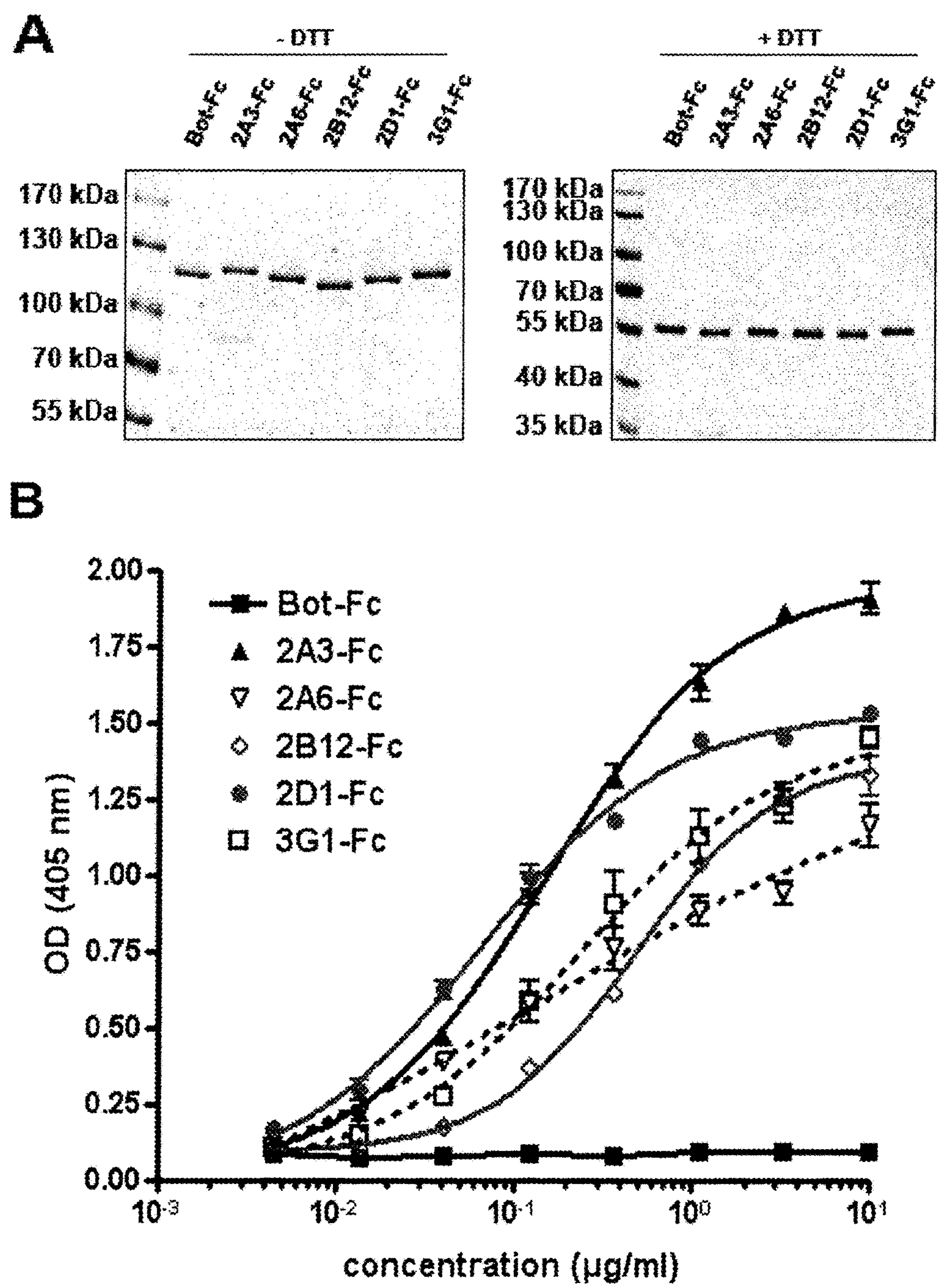

FIG. 2: Conversion of the phage antibody format into a dimeric scFv-Fc format. (A) SDS-PAGE analysis of the 5 anti-KIT ECD scFv-Fcs and the irrelevant scFv-Fc Bot-Fc in non-reducing condition, left panel versus reducing conditions, right panel. ScFv-Fcs are produced in CHO cells and purified on protein A-agarose. (B) ELISA analysis of purified scFv-Fc binding to recombinant c-KIT ECD (see Table 1 for EC50 calculation).

Figure 3:
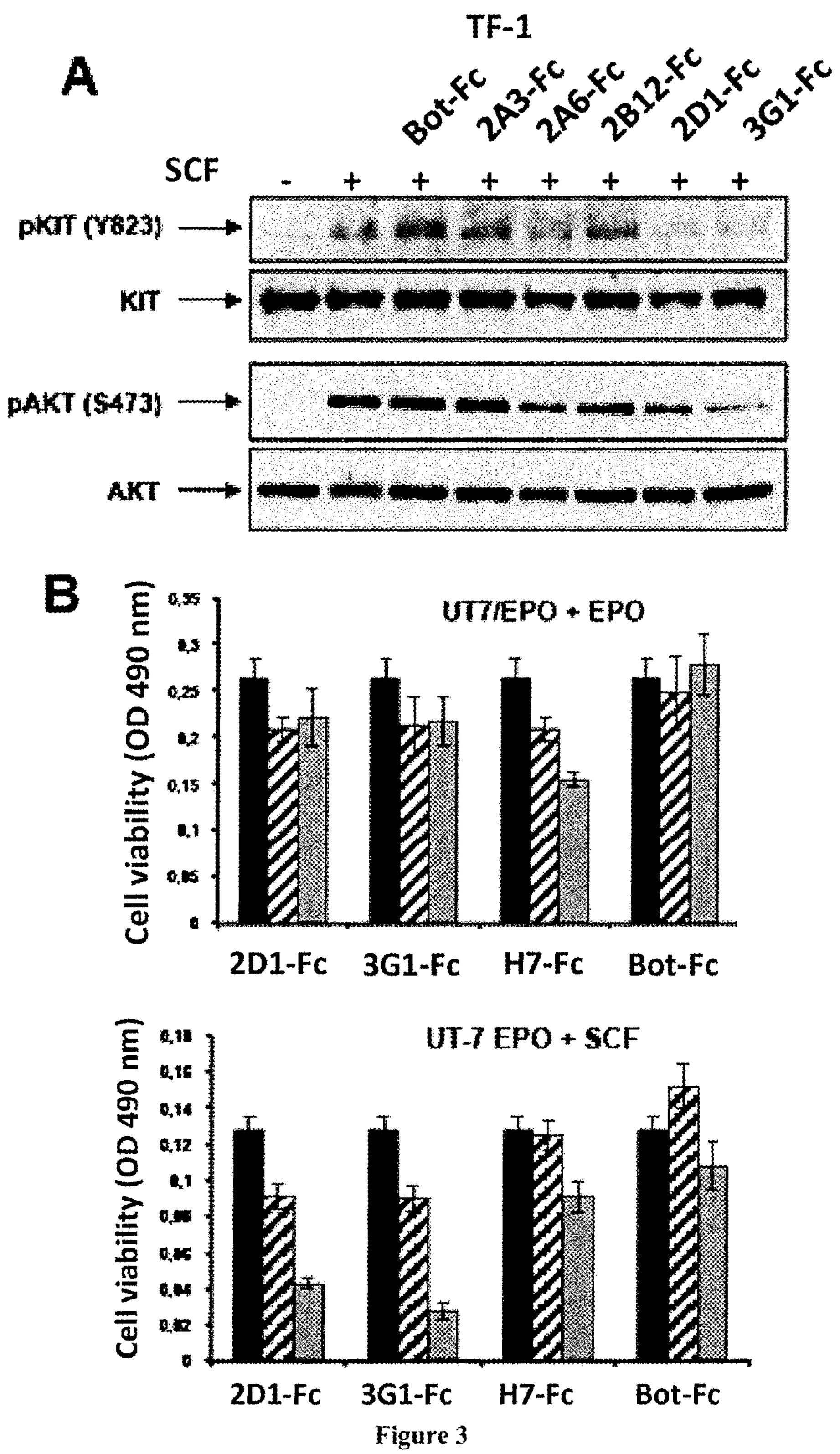

FIG. 3: Antibody interference with wild type KIT signalling. (A) TF-1 cells were starved over night in serum-free medium and incubated with scFv-Fc (10 μg/ml) before 5 minutes stimulation with SCF (250 ng/ml). KIT and AKT phosphorylation were analyzed by Western blot with phospho-specific antibodies. Total KIT and AKT levels were visualized after destripping the membranes and reprobing with anti-KIT and anti-AKT antibodies. (B) UT7/EPO cells were incubated in EPO (upper panel) or CHO-KL supernatant in the presence of anti-KIT antibodies or control antibody as indicated at 5 μg/mL (dashed) or 50 μg/mL (grey) or without antibody (black). Cell viability is expressed in OD at 495 nm.

Figure 4:
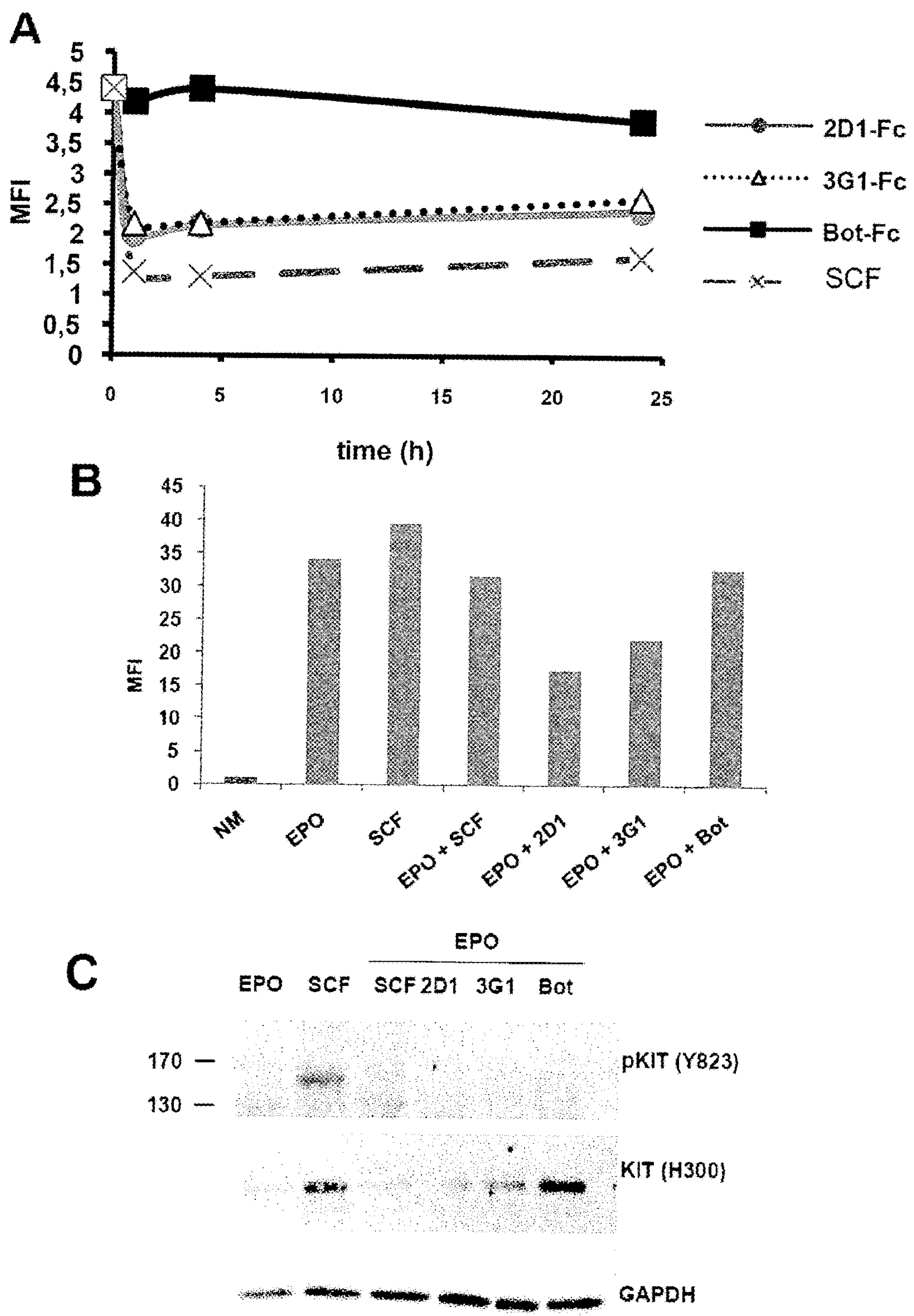

FIG. 4: Antibody modulation of KIT levels in a WT context. KIT levels were estimated by FACS (A, B) using non competing 104D2-anti-KIT antibody. (A) UT7/EPO cells were incubated in complete IMDM medium complemented with EPO for 1, 4, or 24 hrs or with scFv-Fc antibodies (10 μg/mL) or CHO-KL diluted 500 times. (B) UT7/EPO cells were incubated in complete IMDM medium complemented with EPO, alone or with CHO-KL or antibodies (5 or 50 μg/mL) or with CHO-KL (diluted 500 times) alone, as indicated. NM: non marked cells. Results expressed in MFI (Mean fluorescence intensity). Total KIT levels were also determined by Western blot (C) using KIT and phospho-KIT specific antibodies as indicated. Cells were incubated for 5 days before analysis, both with 10 μg/mL of antibodies.

FIG. 5: Antibody modulation of oncogenic KIT. (A) HMC1.1 or HMC1.2 cells were incubated in IMDM 1% serum in the presence of anti-KIT antibodies or control antibody as indicated at 5 μg/mL (light grey) or 50 μg/mL (medium grey) or without antibody (dark grey). Cell viability is expressed in % compared to non treated cells. HMC1.1 or HMC1.2 cells were incubated in IMDM 10% serum in the presence of anti-KIT antibodies or control antibody (10 μg/mL) for 1, 2 or 24 hrs. As indicated and analyzed (B) by FACS using 104D2 anti-KIT antibody or (C) by western blot using anti-KIT and phospho-specific anti-KIT antibodies. (D) Three days treatment with anti-KIT antibodies maintained a low level of KIT on both mastocytoma cell lines.

Figure 6:
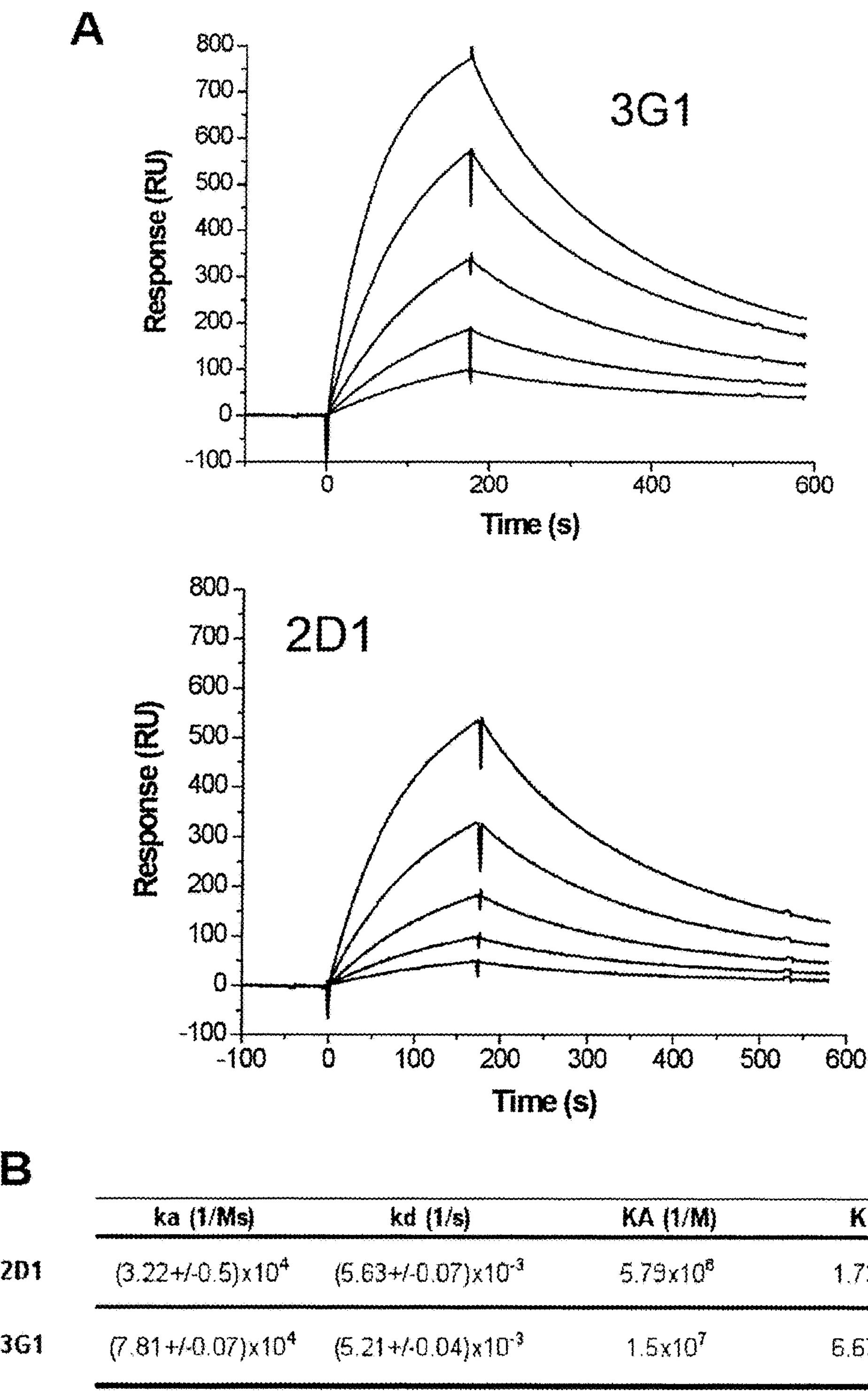

FIG. 6: Analysis of scFv-Fc binding to recombinant KIT-ECD by SPR and determination of kinetics data Kinetic measurements were performed by real time Surface Plasmon Resonance (SPR) analysis using a BIACORE 3000 apparatus (GE Healthcare, Biacore AB, Uppsala, Sweden). Anti-Human IgG (Fc) antibody was immobilized on a flow cell of a CM5 sensor chip following the anti-human capture kit protocol GEHealthcare. A reference flowcell was prepared with the same chemical treatment but without the antibody. All analysis were performed on the two flowcells, at 25° C. at a flow rate of 30 μL/min using HBS-EP (10 mM HEPES pH 7.4, 150 mM NaCl, 3.4 mM EDTA and 0.005% Biacore™ surfactant) as running buffer. Each scFv-Fc was injected at 20 μg/mL over 3 min and followed by an injection (90 μL) of KIT-ECD at different concentrations (from 20 nM to 330 nM). After dissociation step of 400 s, 3M $MgCl_2$ solution was used to regenerate the flowcell surfaces between each run. An irrelevant scFv-Fc (Bot-Fc) was used as negative control. For each scFv a run with buffer instead of KIT-ECD was performed to correct the decaying surface effect. All sensorgrams were corrected by subtracting the signal of the reference flowcell and globally fitted using BIAevaluation 3.2 software. (A) 2D1-Fc and 3G1-Fc sensorgrams were fitted with a Langmuir 1:1 plot. (B) Intrinsic affinity of 2D1 and 3G1 were of 173 nM and 66 nM, respectively.

EXAMPLES

Materials & Methods

Cells and Cell Culture Conditions:

Ba/F3, Ba/F3-KIT and TF-1 cell lines (a gift from Dr. Patrice Dubreuil, INSERM U891, Institut Paoli-Calmettes, Marseille, France) were grown in RPMI (Gibco) containing 10% fetal bovine serum (FBS; PAA) complemented with penicillin/streptomycin (Invitrogen). Ba/F3 and Ba/F3-KIT cells were supplemented with 0.1% conditioned medium from X63-IL-3 (gift from Patrice Dubreuil) and TF-1 with GM-CSF (10 ng/mL) (Invitrogen). UT7/Epo cell line, a subline of UT-7 cells established from UT-7 cells maintained for more than 6 months in the presence of Epo (a gift from Dr. Isabelle Dusanter-Fourt, INSERM U1016, Institut Cochin, Paris, France were grown in IMDM containing FBS and antibiotics as above and supplemented either with EPO (2 U/mL) or SCF. Recombinant human SCF (Cell Signaling) or CHO-KL (a CHO cell line modified to secrete mouse SCF) culture supernatant (a gift of Michel Arock, LBPA, ENS Cachan) were used as a source of SCF depending on the experiments. HMC1.1 and HMC1.2 cell lines that bear a simple mutated V560G KIT allele or a double mutated V560G D816V KIT allele are a gift of Michel Arock, ENS Cachan, Cachan, France). HEK-T cell line was grown in DMEM-FBS 10%-penicillin/streptomycin supplemented with G418 (0.5 mg/mL) (Gibco). All these cells were cultured at 37° C. in a humidified atmosphere enriched in $CO_2$ (5%). Insect cells Sf9 and High Five cells (Invitrogen) were grown at 27° C. in respectively Grace medium or Express Five medium (both from Fisher Scientific) supplemented with 20 mM of L-Glutamine (Invitrogen), penicillin/streptomycin. Grace medium was also supplemented with 10% FBS.

Antibodies and Pharmacological Reagents:

For western blot analysis, anti-KIT extracellular domain (H300) and anti-Erk 2 antibodies were obtained from Santa Cruz Biotechnology Inc., anti-phospho-Akt (Ser 473) and anti-phospho-Erk (Thr 202/Tyr 204) from Cell Signaling, anti-Akt and anti-GAPDH from Millipore and anti-phospho-KIT (Y823) from Invitrogen. Phycoerythrin (PE)-conjugated 104D2 human monoclonal antibody (that does not inhibit SCF binding) (Biolegend) and allophycocyanin (APC)-conjugated 104D2 (BD Biosciences) were used for flow cytometry analysis. Imatinib was a gift from Serge Roche (Centre de Recherche de Biochimie Macromoléculaire—CNRS UMR 5237, Montpellier, France) and Dasatinib was obtained from Santa Cruz.

Recombinant Soluble KIT-ECD Expression and Purification:

Soluble recombinant KIT-ECD was produced in the baculovirus/insect cells system. The KIT-ECD insert in fusion to a 6×His tag was generated by polymerase chain reaction (PCR) amplification of plasmid pSKASapI c-Kit (a gift from Frédéric Subra, LBPA, ENS Cachan, Cachan, France). The amplified product containing BamH I (5' end) and Xba I (3' end) restriction sites was cloned into the vector pGEM-T Easy (Promega) and analyzed by restriction analysis. Kit-ECD BamH I/Xba I was subcloned from pGEM-T Easy into the BD Baculogold™ transfer vector pVL1383 (Beckton Dickinson). Recombinant Kit-ECD baculoviruses were produced in Sf9 cells following the BD Baculogold™ protocol.

To produce soluble recombinant KIT-ECD protein, High Five cells were seeded in serum free medium, infected with recombinant baculoviruses and grown during four days in serum free medium. The culture medium, containing the secreted 6His Tagged was collected and dialyzed in phosphate buffered saline (PBS) before purification with Ni-NTA affinity chromatography (Qiagen). The eluted fraction (elution buffer PBS-Imidazole 250 mM) was concentrated using Amicon concentrator device (Millipore) and buffered into PBS. Total protein concentration was determined by the BCA assay protein quantitation kit (Interchim) and purified proteins analyzed by SDS-PAGE in reducing conditions before Coomassie blue staining.

Selection of KIT-ECD Specific Phage Antibodies:

One hundred μL of KIT-ECD at 50 μg/mL were used to coat a well of a maxisorp 96-well plate (Nunc) at 4° C. over night. The well was saturated with PBS-2% milk during 2 hours at room temperature (RT) before adding $10^{11}$ cfu of the phage library (Sheets et al., 1998) diluted in PBS-2% milk. After 2 hours incubation at RT, the plate was washed 20 times with PBS-Tween 0.1% and 10 times with PBS. Phages were eluted with triethylamine 100 mM and neutralized with a solution of Tris 1M pH 7. Input phages and output phages were titered by infection of *Escherichia coli* TG1 to monitor the selection as described (Marks et al., 1991). Bound phages were amplified for another round of selection. Three rounds of selection were performed. After two and three rounds of selection, soluble scFvs were expressed from single colonies grown in 96-well plates and induced with IPTG 1 mM over night as described (Marks et al., 1991). Crude culture supernatants, containing the soluble scFvs were tested by ELISA for their binding to recombinant KIT-ECD or bovine serum albumin (BSA) (Sigma) as a negative control as described (Schier et al., 1996). The diversity of positive clones on ELISA was determined by sequencing. Positive clones on ELISA were tested for cell binding fluorescence-activated cell sorting (FACS). Two hundred thousand HMC1.2 cells were resuspended in 100 μL of PBS-1% FBS at 4° C. (FACS buffer). One hundred μL of culture supernatant was added to the cells during 2 hours at 4° C. Cells were washed with FACS buffer and scFv binding to cells was detected with an anti-c-myc antibody (9E10; Sigma) followed by goat anti-mouse immunoglobulins (Ig) conjugated to PE (Beckton Dickinson).

Human scFv-Fc Expression and Purification:

To express scFv in fusion with the Fc fragment of human immunoglobulin γ1, scFv cDNA was Nco I/Not I digested and subcloned from phagemid pHEN (Hoogenboom et al., 1991) into pFUSE-hFc2(IL2ss) vector (Moutel et al., 2009), a gift from Frank Perez, CNRS-Institut Curie UMR144, 26 rue d'Ulm, Paris, France). Soluble 110 kD scFv-Fc was produced after transient transfection of HEK-T cells cultivated into 150 $cm^2$ tissue culture dishes. When cells reached 80% confluence, culture medium was removed and replaced with DMEM-penicillin/streptomycin. Transfection was performed using 30 μg of plasmid DNA and 200 μg of polyethylenimine (Polyscience). After 5 days at 37° C., cell supernatant was collected and scFv-Fc was purified with protein A-sepharose column (GE Healthcare). Eluted fractions were diluted in PBS and concentrated on Amicon ultra-4 centrifugal units. scFv-Fc binding botulinum neurotoxin (Bot) (Amersdorfer et al., 1997) and CD71 (H7) produced in the same conditions were used as irrelevant antibody fragment and anti-proliferative positive control.

Analysis of scFv-Fc Binding to Recombinant KIT-ECD by ELISA:

A maxisorp 96-well plate (Nunc) was coated with KIT-ECD (or BSA) diluted at 5 μg/mL in PBS over night at 4° C. Wells were saturated with 300 μL of PBS-BSA 1% during 2 hours at RT. ScFv-Fcs were diluted in PBS-BSA 1% and incubated 2 hours at RT. The plate was washed twice with PBS-Tween 0.05% and once with PBS before adding goat anti-human Fc fragment immunoglobulins conjugated to HRP (Sigma). The plate was revealed with a 2,2'-azino-bis (3-ethylbenzthiazoline-6-sulphonic acid) (ABTS) solution (Roche). Fits and $EC_{50}$ were determined with GraphPad software.

Analysis of scFv-Fc Binding to Cells by Flow Cytometry:

Cell binding was tested by flow cytometry using $2\times10^5$ cells resuspended in 100 μL of FACS buffer (PBS, 1% FCS). All incubations were done at 4° C. to prevent KIT endocytosis. KIT cell surface expression was measured with APC-conjugated anti-KIT. ScFv-Fc binding (10 μg/mL) was detected with goat F(ab')2 fragment anti-human Fc fragment conjugated to PE (Rockland). For competition experiment, cells were preincubated with SCF (1 μg/mL) during 40 minutes before adding the scFv-Fc. Fits and $EC_{50}$ were determined with GraphPad software.

Yeast Display and Affinity Measurement Using Yeast Display:

To improve Kd values of 2D1 and 3G1, we used affinity maturation by light chain shuffling using yeast display. VH sequences were combined to a human VLlambda Library, displayed on yeast using the vector pYD2 (Zhao, Qu et al., 2014), and yeast displaying scFv with higher affinity for KIT were sorted by FACS on the basis of more intense staining in limiting concentrations of antigen. To measure Kd, one million of yeast displaying parental scFv-2D1, affinity matured scFv-2D1C7, scFv-3G1, affinity matured scFv-3G1A2 or an irrelevant scFv, were incubated with biotinylated KIT-ECD, in at least 6 times molar excess, for 1 hour at 4° C. Cells were then put on ice, washed with ice cold FACS buffer and bound antigen was detected with Streptavin conjugated to PE.

Western Blot Analysis:

Cells were starved overnight at 37° C. in serum free medium and incubated for 45 minutes with scFv-Fc (10 μg/mL) before stimulation with recombinant SCF (100 ng/mL) for 5 minutes. Cells were rapidly washed with stop buffer [150 mM NaCl, 50 mM Tris-HCl (pH 6.7), 1 mM EDTA, 2 mM $Na_3VO_4$, 7.5 mM, $Na_4P_2O_7$, 100 mM NaF] and lysed in stop buffer complemented with 1 mM PMSF, 0.25% DOC, 1% NP40 and protease inhibitor cocktail (Roche Diagnostic). Lysates were incubated for 30 minutes on ice and cleared by centrifugation at 13 000×g for 10 minutes at 4° C. Fresh lysates were quantified with BCA assay (Interchim). Thirty μg of proteins were combined in reducing loading buffer [2M Tris (pH 6.7), 4% SDS, 40 mM DTT, 40% glycerol, bromophenol blue], resolved by SDS-PAGE, and transferred onto a nitrocellulose membrane (Amersham Bioscience).

Proliferation Assay:

UT-7 were seeded at $10^4$ cells/well and treated for 4 days with 2D1, 3G1, H7 or Bot irrelevant antibody at 5 or 50 μg/mL used at 5 or 50 μg/mL in the presence of EPO or CHO-KL supernatant diluted 500 times. HMC1.1 and 1.2 were treated the same but for 7 days and with 1% SVF instead of 10% and without cytokines. Cell viability was estimated with MTS assay (PROMEGA) as recommended by the manufacturer.

Internalization Assay:

HMC1.1, HMC1.2, and UT-7/EPO cells were plated at a density of $10^5$ cells/well and incubated with 2D1, 3G1 or Bot-Fc (10 μg/mL) or CHO-KL supernatant (diluted 500 times) in EPO for 1, 4, 24 h or 5 days at 37° C. Cells were washed at room temperature with PBS, fixed for 15 min. at 4° C. (Cytofix, BD biosciences) and stained with the non-competing anti-human KIT 104D2-conjugated to PE/Cy7 and analyzed by FACS as mentioned above.

Results

Selection and Initial Characterization of KIT-ECD-Specific Single Chain Fv (ScFv) Antibodies:

The goal of this study was to isolate fully human KIT-specific antibodies that could inhibit KIT signalling to interfere with cancer cell growth in KIT dependent tumours. The inventors proceeded with an antibody phage-display selection against a recombinant form of human KIT extracellular domain (KIT-ECD, amino acid 26 to 509, P10721 UniProtKB/Swiss-Prot), that they produced in insect cells by baculovirus infection. The purified C-terminal 6His-tagged recombinant KIT-ECD was analyzed on a reducing SDS-PAGE gel (FIG. 1A) and showed a major protein of 60 kD also detected by Western Blot with a commercial antibody directed against the extracellular domain of KIT (H-300, Santa Cruz) (FIG. 1B) which validated the production. For selections, phages were prepared from a $7.0\times10^9$ member human scFv phage naïve antibody library (Sheets, 1998). After 3 rounds of selection (Table 1), 94 clones from the second and third rounds were tested for binding to recombinant KIT-ECD by soluble scFv ELISA. Positive clones (7/94 for the second round; 13/94 for the third round) were sequenced and analyzed, identifying 8 different scFvs that presented different frequency of selection, 2D1 being the most frequent (FIG. 1C). Five of these clones were present since the second round of selection (2D1, 2A3, 2B8, 2B12, 2A6), 3 appeared only after 3 rounds of selection (3G1, 3C12, 3A12). Because these clones had been selected for their affinity for a recombinant form of human KIT produced in insect cells, that have distinct N-glycosylation enzymatic machineries compared to mammalian cells (Shi and Jarvis 2007) we tested whether they could also bind to endogeneous KIT using the highly expressing KIT human mastocytoma cell line HMC1.2. Five antibodies out of eight (2D1, 2A3, 3G1, 2B12, 2A6) in a scFv soluble format, were found to stain HMC1.2 cells—and therefore to detect endogenous KIT with enough sensitivity (FIG. 1D) and processed for further analysis.

TABLE 1

Phage display selection of anti-KIT scFv. Input and output are expressed in pfu (particle forming units).

| | Round 1 | Round 2 | Round 3 |
|---|---|---|---|
| input | $1.2.10^{12}$ | $1.0.10^{12}$ | $2.0.10^{14}$ |
| output | $3.0.10^{4}$ | $1.86.10^{5}$ | $1.33.10^{8}$ |
| output/input | $2.5.10^{-8}$ | $1.86.10^{-7}$ | $6.65.10^{-7}$ |

Conversion into a Bivalent scFv-Fc Format:

In order to increase the avidity for KIT, the 5 anti-KIT monovalent scFvs were converted into a bivalent scFv-Fc format (Moutel et al., 2009) consisting of a fusion at the C-terminal end of the scFv of the hinge domain and the 2 constant domains of the human γl immunoglobulin isotype. Single chain Fv-Fc molecules were produced in HEK cells and purified using protein A affinity chromatography. SDS-PAGE analysis of recovered molecular species showed proteins with the expected 110 kD molecular weight corresponding to covalently linked scFv-Fc homodimers (55 kD each) (FIG. 2A). The inventors next validated the 5 scFv-Fc by testing their binding to recombinant Kit-ECD by ELISA. All scFv-Fc Kd (apparent affinity constant or $EC_{50}$) (Table 2) were in the molar range except for 2A6, for which no saturation of the ELISA signal was obtained at the maximal concentration tested (10 μg/mL or 91 nM) suggesting a poor binding capacity. Within the antibodies tested, 2D1 displayed the lowest apparent Kd ($EC_{50}$ of 0.6 nM or 0.067 μg/mL) (FIG. 2B). Therefore, scFv reformatting into scFv-Fc and production in mammalian cells instead of bacteria conserved antibody specificity since all scFv-Fc bound to the receptor while an irrelevant antibody fragment of the same format produced in the same conditions did not.

TABLE 2

Concentration of scFv-Fc antibody format giving 50% of maximal OD at 405 nm. Fits and $EC_{50}$ were determined with GraphPad software after FIG. 2B.
EC50 (μg/ml)

| 2A3-Fc | 2A6-Fc | 2B12-Fc | 2D1-Fc | 3G1-Fc |
|---|---|---|---|---|
| 0.150 | >0.2 | 0.480 | 0.067 | 0.240 |

ScFv-Fc Binding on Cells and Competition with SCF Binding to KIT:

The inventors tested the binding of the 5 anti-KIT scFv-Fc to cell lines expressing different levels of surface KIT as detected by the commercial 104D2 mouse mAb (Broudy et al., 1998) including the human mastocytoma HMC1.2 cell line, the erythroleukemic TF-1 cell line and the murine pro-B Ba/F3 cell line modified to express human KIT (medium levels of KIT, Ba/F3-KIT cell line). The parental murine Ba/F3 cell line, that do not express endogenous mouse KIT, was used as a negative control. FACS analysis showed KIT detection on HMC1.2 and TF-1 cells with all 5 anti-KIT scFv-Fc (10 μg/mL), 2A6-Fc showing lower staining on both cell lines. 2B12, 2D1 and 3G1-Fc stained Ba/F3-KIT cells, while staining was negative on the Ba/F3 cell line, confirming KIT specificity. Unexpectedly, despite strong staining of HMC12 cells 2A3 did not stain Ba/F3 KIT cell line.

They tested then if SCF could block the binding of the antibodies to KIT. High KIT expressing HMC1.2 cells were maintained at 4° C. and incubated with SCF (1 μg/mL) or not before adding the anti-KIT scFv-Fc (10 μg/mL) and bound antibodies were detected by FACS. 2A6, 2D1 and 3G1-Fc binding was significantly reduced by a pre-incubation with SCF suggesting that SCF and antibodies may bind overlapping sites on the receptor. Alternatively, SCF could induce a conformational change in KIT that prevents further binding of the anti-KIT antibodies.

Antibody Interference with Wild Type KIT Signalling:

Because KIT activation results from dimerization induced by SCF binding, anti-KIT scFv-Fc might activate KIT in an agonistic manner due to their dimeric format. To test this hypothesis the erythroleukemic cell line TF-1, that displays 2 alleles of wild type KIT, was cultivated overnight in serum free and GM-CSF free medium before treatment with the scFv-Fc (10 μg/mL). Western Blot analysis of crude protein extracts showed that none of the 5 scFv-Fc induced KIT phosphorylation of tyrosine 823, located in the activation loop of the kinase domain, required for KIT full kinase activity (Agarwal et al. 2013). Alternatively, they tested whether the scFv-Fcs could prevent KIT stimulation by SCF. Starved TF-1 cells were incubated with scFv-Fc (10 μg/mL, 45 min.) before stimulation with recombinant SCF (100 ng/mL, 10 min). Western blot revealed that 2A6, 2D1 and 3G1-Fc inhibited SCF-induced KIT phosphorylation on tyrosine 823, 2D1 and 3G1-Fc being the most effective, while an irrelevant identical antibody format did not (FIG. 3A). AKT phosphorylation was also reduced by the same antibodies, with stronger reduction with 2D1 and 3G1-Fc than with 2A6A-Fc. Therefore, in the rest of the study, the inventors focused on 2D1 and 3G1-Fc antibody formats.

To investigate if the antagonistic effect of 2D1 and 3G1-Fc on SCF-dependent KIT signalling translated into functional effects, they used the UT-7/EPO cell line which is dependent on either EPO or SCF for its proliferation in vitro (Erickson-Miller, Pelus et al. 2000). Antibodies alone did not sustain the growth of UT-7/EPO cells in the absence of EPO or SCF (not shown) but did decrease cell viability in a dose dependent manner when cells were cultivated with SCF but not with EPO, while an anti-TfR1 (transferring receptor 1) antibody, in the same format, decreased cell viability both in EPO and SCF cultivated cells and an irrelevant antibody had no effect (FIG. 3B). Additionally, like in TF-1 cells, 2D1 and 3G1-Fc inhibited downstream effectors pathways associated with KIT signalling (phosphorylation of KIT on tyrosine 823, phosphorylation of AKT and ERK) and when used alone did not stimulate KIT signalling in UT-7/EPO cell line (not shown).

These results show that the KIT specific 2D1 and 3G1-Fc inhibit SCF-dependent KIT signalling in cells expressing wild type KIT and that this effect is likely in part due to do the blockade of SCF binding to KIT. To complete the characterisation of 2D1 and 3G1-Fc, their intrinsic affinity for KIT-ECD was determined by surface Plasmon resonance and was estimated to 173 and 66 nM, respectively) (FIG. 6).

Fine Epitope Mapping of 2D1 and 3G1:

KIT extracellular domain (ECD) is structured in 5 Ig domains. From the crystal structure, it is know that dimeric KIT ligand binding to Domain 2 and 3 induces the dimerisation of KIT at the cell surface, homotypic interactions between domains 4 and domains 5 of each member of a KIT dimer that induce a twist in the intracellular domain, favoring the activation of intracellular tyrosine kinase. of the receptor (Yuzawa S, et al. 2007). To identify clearly to which domains 2D1 and 3G1 antibodies bind, we displayed full length or truncated forms of KIT at the surface of yeast. The antigen of interest is fused to the yeast surface Aga2 protein. A flexible linker between the antigen of interest and Aga2 ensures accessibility of the antigen to the antibodies. Domains of human EGFR, a member of the Tyrosine kinase receptor family, like KIT, have been functionally displayed on the yeast surface and used to map Ab epitopes (Johns, Adams et al. 2004). Full length human KIT extracellular domain (amino acids 26-519; nucleotide 76 to 1542, cDNA sequence reference NM_001093772.1) was displayed on yeast using the yeast expression vector pYD2 as described in Zhao, Qu et al. 2014, Truncated forms of either D1-D3 (amino acids 26-307, nucleotides 76 to 921), D4-D5 (amino acids 308-516, nucleotides 922 to 1548), D4 (amino acids 308-409, nucleotides 922 to 1227) and D5 (amino acids 410-516, nucleotides 1228 to 1548), truncated forms were also expressed. Yeast expressing the different domains were stained with 2D1 or 3G1 scFv-Fc followed by anti-human-IgG conjugated to Phycoerythrin (PE) or with the commercial monoclonal anti-human KIT antibody 104D2 conjugated to Phycoerythrin (PE)-Cyanin 7 (PE-Cy7) described to not inhibit binding of SCF to KIT (Biolegend).

Anti-Kit antibodies 2D1 and 3G1-scFv-Fc (15 nM) or 104D2 conjugated to PE-Cy7 (1.5 nM) were incubated at room temperature for 1 hr. with 1 million of yeast displaying either KIT domains 1 to 3 (KIT-D1-3), KIT domains 4 and 5 (KIT-D4-5) or full length KIT extracellular domain (KIT-D1-5). 2D1 and 3G1-scFv-Fc binding was detected with anti-Hu-Fc Ig conjugated to PE. 2D1 and 3G1 binds to KIT D4-D5 whether 104D2 binds to KITD13. Anti-Kit soluble 2D1 and 3G1 scFv-Fc were incubated with KIT domains D4 or KIT domain D5 displayed on yeast. Both 2D1 and 3G1 bind specifically to domain D5 of KIT. Binding of 104D2 conjugated to PE-Cy7(1.5 nM) on KIT-D1-5 displayed on yeast was tested in the presence of 2D1 and 3G1-scFv-Fc (15 nM). Neither 2D1 nor 3G1 inhibit 104D2 binding to KIT displayed on yeast.

To explore if 2D1 and 3G1 bound overlapping epitope, scFv-2D1 was displayed on yeast. One million of yeast displaying 2D1 scFv were incubated with recombinant biotinylated Kit-ECD produced in insect cells (100 nM) alone or in the presence of soluble 2D1 or 3G1 scFv-Fc (15 nM or 1.5 nM) at room temperature for 1 hour. Bound antigen was detected using streptavidin conjugated to PE. As expected, soluble 2D1-scFv-Fc inhibited the binding of KIT to scFv-2D1 displayed on yeast. Notably, 3G1 inhibited also the binding of KIT to 2D1, showing that 3G1 and 2D1 bind overlapping epitopes on D5.

Therefore, 2D1 and 3G1 likely inhibit KIT wild type KIT signaling by inhibition of homotypic interactions between the membrane-proximal domain of KIT-D5 after binding of SCF, that are crucial for receptor activation (Yuzawa S, et al. 2007).

Antibody Modulation of KIT Levels in a WT Context:

In a therapeutic orientated strategy, one way to reduce KIT signalling in cancer cells, would be to decrease KIT levels at the cell surface to reduce its access to SCF and/or induce its degradation. SCF binding to KIT at the cell surface has been shown to rapidly induce internalization and degradation of KIT, its reexpression at the cell surface requiring neo synthesis of KIT (Shimizu, Ashman et al. 1996). The inventors wondered if the 2D1 and 3G1-Fc, even though they do not induce KIT phosphorylation, would trigger KIT internalization and degradation like SCF and would have a long term effect on KIT levels at the cell surface.

The effect of antibody treatment on KIT surface level was analyzed by FACS using the 104D2 anti-KIT mAb, that does not interfere with SCF, and with 2D1 and 3G1 for KIT binding. First, they analysed short term effect of anti-KIT compared to SCF treatment. Addition of 2D1 or 3G1-Fc to UT-7/EPO cultivated in the presence of EPO (and no SCF) rapidly initiated strong KIT surface down-regulation with kinetics similar than with SCF though quantitatively lower decrease was obtained with the antibodies than with SCF throughout the treatment, (50% versus 70%, respectively, after 1 hour) (FIG. 4A). Cell surface down-regulation remained stable after 24 hrs, both in the presence of antibodies or ligand even though after 2 hours of treatment, KIT surface levels started to increase slightly due, at least partially, to increased synthesis since this increase was inhibited by CHX (not shown). Therefore, 2D1 and 3G1-Fc induced KIT internalization without inducing KIT downstream signalling. Then, they analyzed long term effect of scFv-Fc treatment (FIG. 4B). KIT surface levels of UT7/EPO cells cultivated in EPO were decreased after 5 days of treatment with 2D1 or 3G1-Fc while a SCF treatment (in addition to EPO), did not modulate KIT levels. To note, UT-7/EPO cells had a higher level of surface KIT when cultivated in SCF compared to EPO as a source of cytokine, consistent with data previously published (Kosmider, Buet et al. 2009) (FIG. 4B). They also measured total level of KIT by Western blot upon antibody short or long treatment of UT7/EPO cells cultivated with EPO. After 24 hours KIT total levels were not drastically affected neither with 2D1 and 3G3-Fc nor with SCF treatment but long term treatment reduced drastically KIT levels both with antibodies or SCF (FIG. 4C).

Therefore, without stimulation KIT downstream effector pathways, 2D1 and 3G1-Fc, induce long term cell surface down regulation of KIT on the UT-7/EPO cell line.

To confirm that 2D1 and 3G1-Fc KIT surface downregulation was kinase activity independent, imatinib was combined to anti-KIT 2D1 or 3G1-Fc on UT-7/EPO cells cultured with EPO. Interestingly, TKI had an additive effect on KIT surface down regulation while on the contrary, imatinib inhibited SCF-induced KIT surface level decrease, as expected, as activation of KIT is coupled to its degradation (Yee, Hsiau et al. 1994). Imatinib treatment alone decreased KIT surface levels, as recently published (D'Allard, Gay et al. 2013). These data show that 2D1 and 3G1-Fc decrease KIT surface independently of KIT kinase activity and that imatinib treatment enhances this decrease by an unknown mechanism.

Figure 5A:
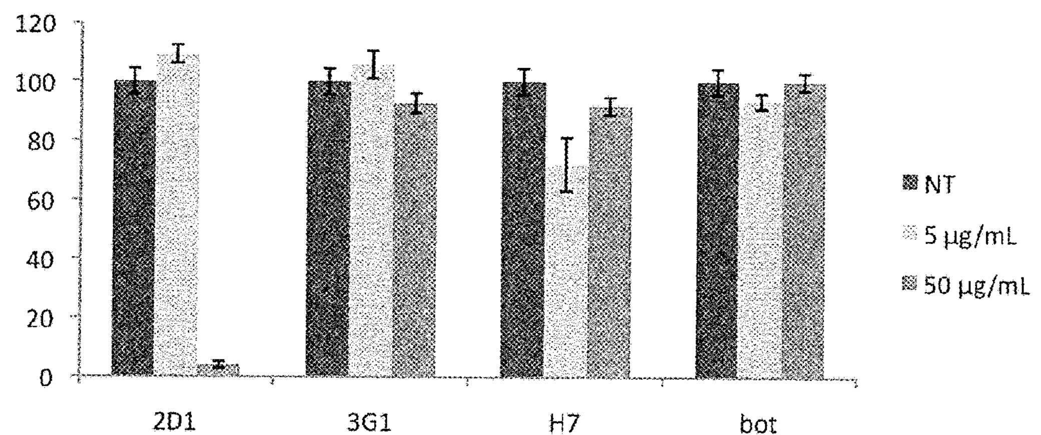
Figure 5A:
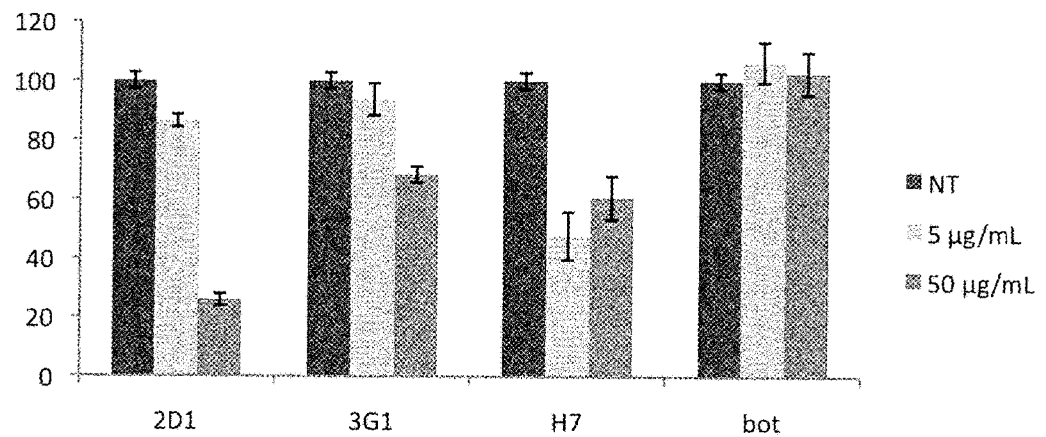
Figure 5B:
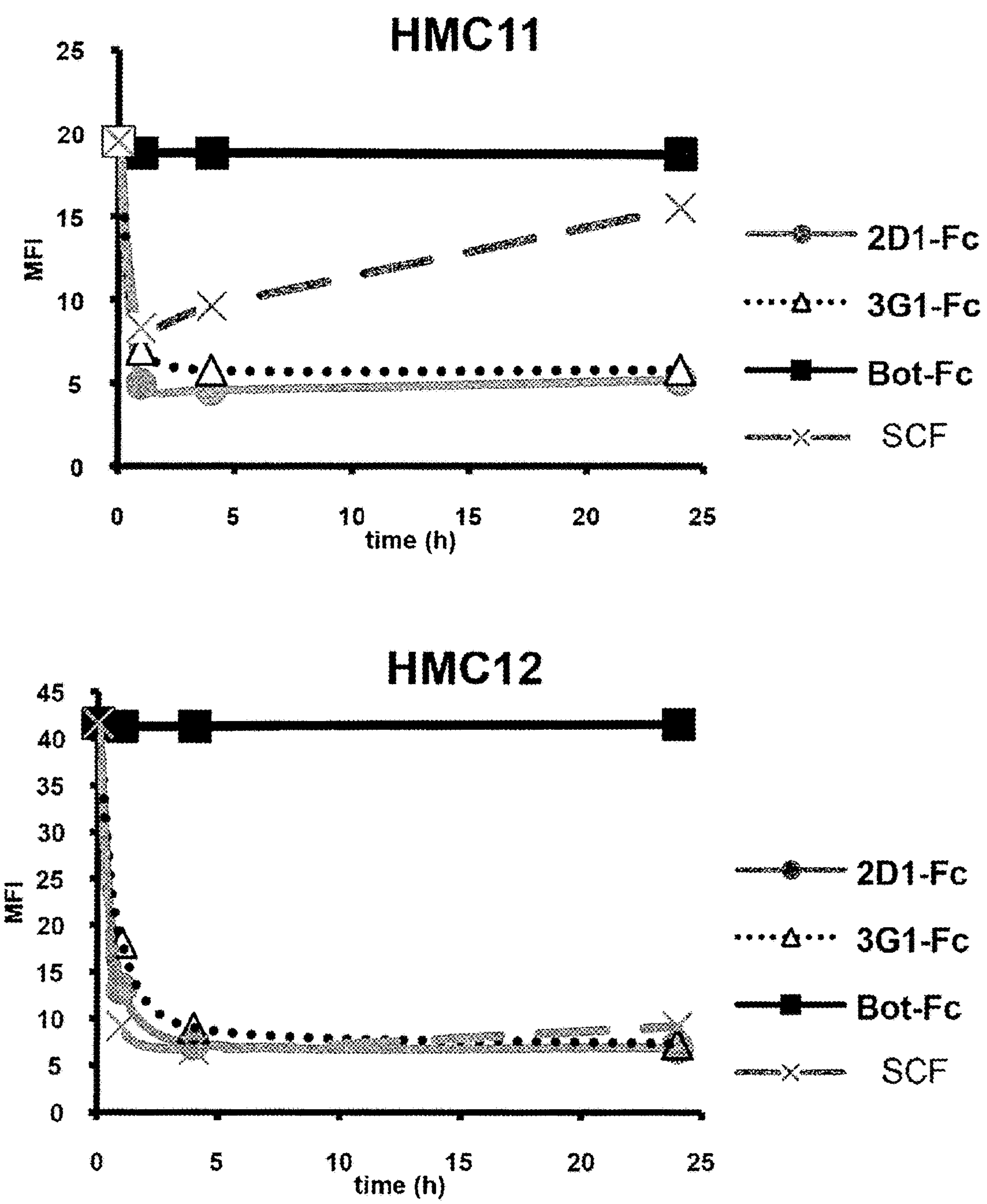
Figure 5C:
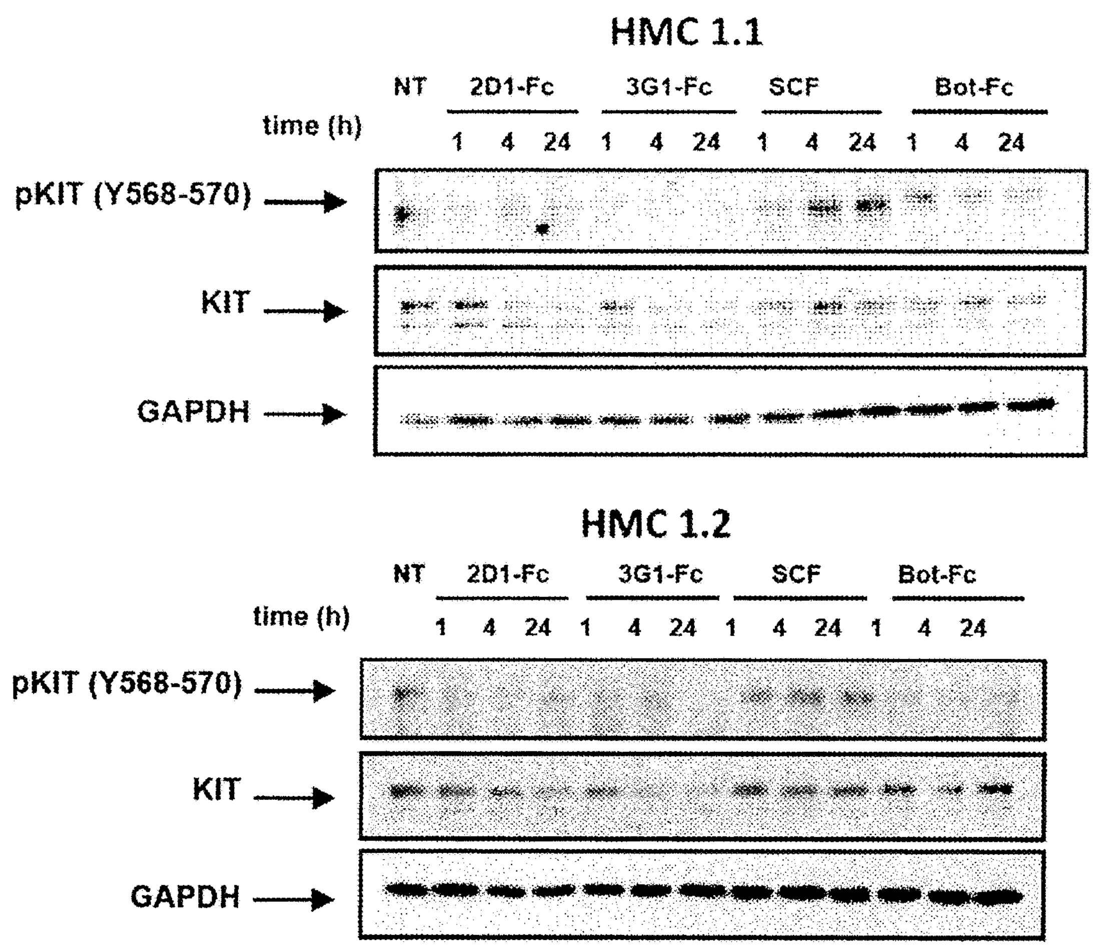
Figure 5D:
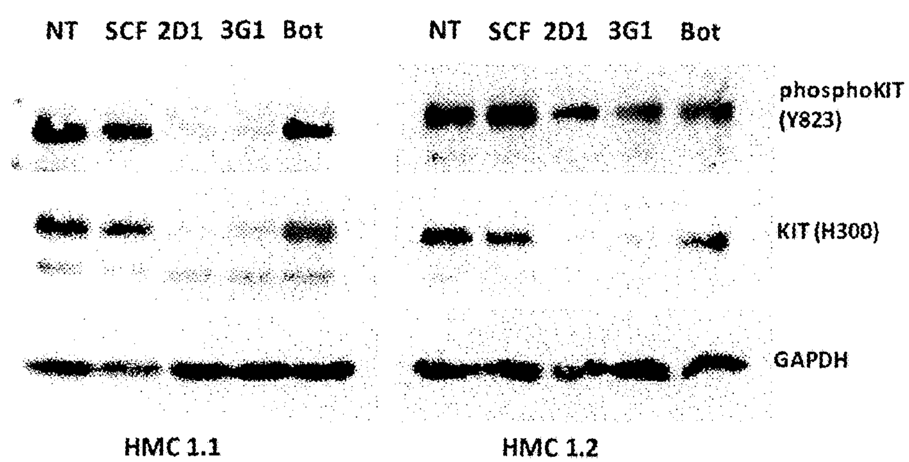

Antibody Interference with Oncogenic KIT Activation and Surface Levels:

KIT signalling of oncogenic KIT mutants is independent of SCF. Since 3G1 and 2D1-Fc were able to induce KIT internalization and degradation in UT-7 cell, the inventors tested their effect on the mastocytoma HMC1.1 (KITV560G) and HMC1.2 (KIT V560G D816V) cancer cell lines that express constitutively active KIT oncogenic mutants and that depend on KIT signalling for growth and survival. As expected, imatinib and dasatinib TKI were toxic to HMC1.1 cells but only dasatinib was toxic to HMC1.2 cells due to the resistance of the D816V mutant to imatinib. HMC1.1 and HMC1.2 cell lines were treated with the antibodies at 5 and 50 μg/mL for 7 days and cell viability was quantified. At the maximal concentration, both 2D1 and 3 G1-Fc decreased the viability of HMC1.1 and HMC1.2 cells (FIG. 5A) while irrelevant antibody had no effect. Decreased viability was associated with strong KIT degradation and decreased phosphorylation of KIT tyrosines 568 and 570. Surface level KIT modulation kinetics was analyzed like on UT-7/EPO cell line. In both mastocytoma cell lines, after 1 hour, both 2D1 and 3G1 induced a strong decrease of KIT levels similar to SCF treatment (FIG. 5B). A low level of surface KIT was maintained for 24 hrs in all conditions except on HMC1.1 cell line treated with SCF were KIT was re-expressed at the cell surface and almost reached initial level after 24 hr. Neo synthesis was implicated in the re-appearance of KIT of HMC1.1 cells treated with SCF at the cell surface in HMC1.1 since it was not observed in the presence of CHX. These observations reveal a different regulation of traffic/synthesis of KIT in the 2 cell lines likely related to distinct mutation of KIT. Decrease of cell surface KIT on anti-KIT treated cells was associated with decrease of total KIT levels as seen by Western blot (FIG. 5C). Three days treatment with antibodies maintained a low level of KIT on both mastocytoma cell lines (FIG. 5D).

Altogether these data show that, the 2D1 and 3G1-Fc inhibit cell viability of mastocytoma cell lines including cells that are resistant to imatinib due to the presence of the D816V mutation on KIT. On these cells, that are dependent of oncogenic KIT signalling for their growth and survival, 2D1 and 3G1-FC induce a strong KIT degradation, likely reducing oncogenic downstream signalling.

Affinity Maturation:

Bivalent scFv-2D1 and 3G1 binding on monovalent KIT-ECD adsorbed on plastic by ELISA resulted in an EC50 of 0.067 μg/mL and 0.240 μg/mL, respectively corresponding to an apparent dissociation constant Kd of 0.61 and 2.18 nM, respectively. The affinity of 2D1 and 3G1 measured by Biacore showed that intrinsic affinity of 2D1 and 3G1 paratope for KIT was in the 100 nM range with kinetic $k_{on}$, constant of 3.22 and 7.81 $10^4$ M-1.s-1 and $k_{off}$ of 5.63 and 5.21 $10^{-3}$ s-1. To improve intrinsic Kd values, 2D1 and 3G1 were affinity matured by light chain shuffling using yeast display. VH sequences were combined to a human VLlambda Library, displayed on yeast, and yeast displaying scFv with higher affinity for KIT were sorted by FACS on the basis of more intense staining in limiting concentrations of antigen.

A variant of 2D1, 2D1-C7 and a variant of 3G1, 3G1-A2, displaying increased affinity compared to the parental antibody were obtained. Affinity matured 2D1 scFv-Fc (2D1-C7) consisted in a scFv with the same VH sequence and 5 substitutions and 2 additions of aminoacids in the VL gene. In the original VL-2D1 sequence, 6 of the 7 modifications occurred in the CDR2 and the CDR3. Affinity matured 3G1 scFv-Fc (3G1-A2) consisted in a scFv with the same VH sequences, 3 substitutions in VL in addition to a complete modification of the CDR3.

Affinity was considerably increased with saturation reached with 10 nM concentrations of Ag and intrinsic Kd of 4.2+/−1.2 nM and 1.7+/−0.5 nM, respectively for 2D1-C7 and 3G1-A2.

Discussion:

Obtention of KIT Antagonist Antibodies:

Phage antibody libraries have become useful tools to isolate and develop antibodies suitable for diagnostic or therapeutic uses. Most of the antibodies selected from combinatorial libraries expressed on phage have been isolated using purified antigens immobilized on artificial surfaces. This approach might select antibodies that recognize or not the native protein in a physiological context. In this work, the inventors generated 8 antibodies against the extracellular domain of KIT produced in insect cells (FIG. 1). The antibody 2D1-Fc represented 40% of the binders recovered in this selection. Three out of 8, when expressed as soluble monovalent scFvs did not detect endogenous KIT on HMC1.2 cells even though they bound recombinant KIT may be due to a low affinity for KIT or to the recognition a N-glycosylation specific to insect cells (Shi and Jarvis 2007). When reformatted into a bivalent scFv-Fc format and produced in mammalian cells, all 5 antibodies bound to high KIT expressing HMC1.2 cells but 2 did not detect KIT on Ba/F3 cells transfected to express WT human KIT cells. This lack of binding is likely due to lower affinity for KIT in the case of 2A6 (Table 2) but the reason is unclear for 2A3 since 2A3 affinity for KIT (Table 1) and 2A3 staining intensity of KIT on TF-1 and HMC12 cells was in the same order of magnitude than for the other 3 antibodies 2B12, 2D1 and 3G1 that indeed detect KIT on Ba/F3-KIT cells.

KIT dimerization induced by SCF (when KIT is in its wild type form) is required to cross phosphorylate its intracellular domain. Because of the scFv-Fc dimeric format we used, we expected a possible agonistic activity of this format on KIT. None of the 5 anti-KIT scFv-Fc, however, induced KIT phosphorylation or were able to maintain the growth of SCF-dependent cell lines (TF-1, UT-7/EPO) in cytokine free medium. On the contrary, 3 antibodies inhibited SCF-dependent KIT phosphorylation (2A6, 2D1 and 3G1-Fc) and competed with SCF for binding to KIT. The best competitors (2D1 and 3G1-Fc) reduced cell viability of UT-7/EPO cells when grown in the presence of SCF as a source of cytokine demonstrating that they specifically and efficiently inhibited KIT signalling. Therefore this strategy allowed the isolation of antibodies that blocked SCF access to KIT and further downstream signalling. Interestingly, 2D1 and 3G1 likely inhibit KIT wild type KIT signaling by inhibition of homotypic interactions between the membrane-proximal domain of KIT-D5 after binding of SCF, that are crucial for receptor activation (Yuzawa S, et al. 2007). No inhibitory antibody binding to D5 of KIT has been yet described.

KIT (WT and Mutated Isoforms) Modulation:

Since wild type KIT was not activated by the anti-KIT antibodies 2D1 and 3G1-Fc, the inventors addressed the question of the modulation of KIT at the cell surface and its degradation upon antibody treatment. Interestingly, internalization of KIT was observed independently of a wild type or mutated context (either catalytic or juxta membrane mutant) but strong degradation was observed only in mutant backgrounds (FIGS. 4 and 5).

In normal mastocytes, upon SCF stimulation, KIT is rapidly degraded (within hours) and its surface expression totally renewed at the cell surface after 48 hrs exclusively by neosynthesis (Shimizu, Y J I 1996). No recycling has been described for KIT. Receptor kinase activity is required for SCF-induced efficient degradation of KIT which involves ubiquitinylation of KIT and both lysosomal and proteasome pathways and (Yee, Hsiau et al. 1994). Oncogenic mutated forms of KIT display a modified subcellular localization compared to wild type KIT with a important fraction of the protein being linked to intracellular vesicles and able to initiate signalling from inside the cell (Schittenhelm, Aichele et al. 2003). It is unclear if KIT mutants expression at the cell surface is required for oncogenic signalling in vivo and how mutated KIT interacts with wild type KIT, that is co-expressed with KIT in cancer cells (Theou, Tabone et al. 2004) and influences wild type KIT intracellular trafficking. KIT levels at the cell surface, independently of variations in neosynthesis, depends on KIT catalytic activity since inhibition of KIT mutant activity with pharmacological drugs relocalizes KIT at the cell surface within minutes (Bougherara et al, 2009). KIT surface levels also depends on the occupation of the ATP binding site of the intracellular kinase domain of KIT (Kosmider O. et al, 2013) since blocking of the ATP pocket of WT KIT with imatinib, in the absence of stimulation by SCF, induced internalisation and degradation of inactivated KIT. Here treatment with 2D1 or 3G1-Fc induced KIT internalization but not degradation of KIT. Recently, Edris and colleagues, used the anti-KIT antibody SR1 (Ashman, Buhring et al. 1994, Papayannopoulou, Brice et al. 1991) and did not observed degradation of KIT after long time treatment (Edris, Willingham et al. 2013) in GIST cell line presenting various KIT alleles, including juxtamembrane mutant with or without additional gatekeeper mutation. Therefore, 2D1 and 1G1 anti-KIT antibodies have a different action than SR1 antibody. The targeting of KIT domain 5 by 2D1 and 3G1 induces the internalization of both wild type and oncogenic KIT and the degradation of oncogenic KIT while sparing WT KIT.

Experiments are in progress to combine TKI and 2D1 or 3G1-Fc treatment to unravel a potential synergistic effect on KIT inhibition both in a wild type or mutated setting.

The association of anti-KIT targeting domain D5 and pharmacological inhibitor of KIT activity could be an approach enhance inhibition of KIT activity.

UT7 leukemic cells grown in the presence of IMDM complemented with serum and EPO were treated with Imatinib 1 μM and/or 10 μg/mL of 2D1 or 3G1 scFv-Fc for 4 hrs at 37°. Cells were then kept at 4° C., stained with 104D2 anti-KIT antibody coupled to PE-CY7 and analyzed by FACS. As expected, a single treatment with the TKI Imatinib reduced KIT level at the cell surface (D'Allard et al, 2013). The association of anti-KIT antibody and TKI treatment enhanced the reduction of KIT surface levels compared to single treatment, while irrelevant antibody (Bot-Fc) had no effect.

Toxicity

Compared to small inhibitors, antibody based immunotherapy of tumours have the advantage to recruit immune effectors through the Fc part of the antibody (Adams and Weiner 2005). The scFv-Fc antibody format of this study (that display a human gamma1 Fc region) can theoretically recruit immune effectors like NK cells or mediate cell lysis through the complement cascade but we have not observed scFv-Fc anti-KIT mediated ADCC and CDC on high KIT expressing HMC1.1 and HMC1.2 cells using 2D1 and 3G1-Fc. So targeting KIT with antibody devoid of effector functions but interfering with KIT signalling may be the best KIT targeting strategy to avoid secondary effects and still reach therapeutic efficiency in KIT dependent cancers.

To conclude, the inventors showed that 2D1 and 3G1-Fc inhibit cell viability of mastocytoma cell lines including cells that are resistant to imatinib due to the presence of the D816V mutation on KIT. On these cells, which are dependent of oncogenic KIT signalling for their growth and survival, 2D1 and 3G1-Fc induce a strong and long term KIT degradation, likely reducing oncogenic downstream signalling. Affinity improved variant of 2D1-C7 and 3G1-A2 should have increased inhibitory activity compared to 2D1 and 3C7. Moreover, these antibodies do not elicit immune effector function therefore anticipating limited toxicity in vivo.

REFERENCES

Throughout this application, various references describe the state of the art to which this invention pertains. The disclosures of these references are hereby incorporated by reference into the present disclosure.

Adams, G. P. and L. M. Weiner (2005). "Monoclonal antibody therapy of cancer." *Nat Biotechnol* 23(9): 1147-1157.

Agarwal, S., J. U. Kazi, et al. (2013). "Phosphorylation of the activation loop tyrosine 823 in c-Kit is crucial for cell survival and proliferation." *J Biol Chem* 288(31): 22460-22468.

Antonescu, C. R., P. Besmer, et al. (2005). "Acquired resistance to imatinib in gastrointestinal stromal tumor occurs through secondary gene mutation." *Clin Cancer Res* 11(11): 4182-4190.

Ashman, L. K., H. J. Buhring, G. W. Aylett, V. C. Broudy and C. Muller (1994). "Epitope mapping and functional studies with three monoclonal antibodies to the c-kit receptor tyrosine kinase, YB5.B8, 17F11, and SR-1." J Cell Physiol 158(3): 545-554.

Bernex, F., P. De Sepulveda, et al. (1996). "Spatial and temporal patterns of c-kit-expressing cells in WlacZ/+ and WlacZ/WlacZ mouse embryos." *Development* 122(10): 3023-3033.

Blechman, J. M. and Y. Yarden (1995). "Structural aspects of receptor dimerization. c-kit as an example." *Ann N Y Acad Sci* 766: 344-362.

Broudy, V. C. (1997). "Stem cell factor and hematopoiesis." *Blood* 90(4): 1345-1364.

Broudy, V. C., N. L. Lin, et al. (1998). "Analysis of c-kit receptor dimerization by fluorescence resonance energy transfer." *Blood* 91(3): 898-906.

D'Allard, D., J. Gay, et al. (2013). "Tyrosine kinase inhibitors induce down-regulation of c-Kit by targeting the ATP pocket." *PLoS One* 8(4): e60961.

Demetri, G. D., M. von Mehren, et al. (2002). "Efficacy and safety of imatinib mesylate in advanced gastrointestinal stromal tumors." *N Engl J Med* 347(7): 472-480.

Edris, B., S. B. Willingham, et al. (2013). "Anti-KIT monoclonal antibody inhibits imatinib-resistant gastrointestinal stromal tumor growth." *Proc Natl Acad Sci USA* 110(9): 3501-3506.

Emens, L. A. (2005). "Trastuzumab: targeted therapy for the management of HER-2/neu-overexpressing metastatic breast cancer." *Am J Ther* 12(3): 243-253.

Erickson-Miller, C. L., L. M. Pelus, et al. (2000). "Signaling induced by erythropoietin and stem cell factor in UT-7/Epo cells: transient versus sustained proliferation." *Stem Cells* 18(5): 366-373.

Heinrich, M. C., D. J. Griffith, et al. (2000) "Inhibition of c-kit receptor tyrosine kinase activity by STI 571, a selective tyrosine kinase inhibitor." *Blood* 96(3): 925-932.

Hibi, K., T. Takahashi, et al. (1991). "Coexpression of the stem cell factor and the c-kit genes in small-cell lung cancer." *Oncogene* 6(12): 2291-2296.

Hodi, F. S., C. L. Corless, et al. (2013). "Imatinib for melanomas harboring mutationally activated or amplified KIT arising on mucosal, acral, and chronically sun-damaged skin." *J Clin Oncol* 31(26): 3182-3190.

Ikeda, H., Y. Kanakura, et al. (1991). "Expression and functional role of the proto-oncogene c-kit in acute myeloblastic leukemia cells." *Blood* 78(11): 2962-2968.

Johns T G, Adams T E, Cochran J R, Hall N E, Hoyne P A, et al. (2004) Identification of the epitope for the epidermal growth factor receptor-specific monoclonal antibody 806 reveals that it preferentially recognizes an untethered form of the receptor. *J Biol Chem* 279: 30375-30384

Kemmer, K., C. L. Corless, et al. (2004). "KIT mutations are common in testicular seminomas." *Am J Pathol* 164(1): 305-313.

Kitayama, H., Y. Kanakura, et al. (1995). "Constitutively activating mutations of c-kit receptor tyrosine kinase confer factor-independent growth and tumorigenicity of factor-dependent hematopoietic cell lines." *Blood* 85(3): 790-798.

Kosmider, O., D. Buet, et al. (2009). "Erythropoietin down-regulates stem cell factor receptor (Kit) expression in the leukemic proerythroblast: role of Lyn kinase." *PLoS One* 4(5): e5721.

Krystal, G. W., S. J. Hines, et al. (1996). "Autocrine growth of small cell lung cancer mediated by coexpression of c-kit and stem cell factor." *Cancer Res* 56(2): 370-376.

Krystal, G. W., S. Honsawek, et al. (2000). "The selective tyrosine kinase inhibitor STI571 inhibits small cell lung cancer growth." *Clin Cancer Res* 6(8): 3319-3326.

Lennartsson, J. and L. Ronnstrand (2012). "Stem cell factor receptor/c-Kit: from basic science to clinical implications." *Physiol Rev* 92(4): 1619-1649.

Lev, S., J. Blechman, et al. (1993). "Interspecies molecular chimeras of kit help define the binding site of the stem cell factor." *Mol Cell Biol* 13(4): 2224-2234.

Levina, V., A. Marrangoni, et al. (2010). "Elimination of human lung cancer stem cells through targeting of the stem cell factor-c-kit autocrine signaling loop." *Cancer Res* 70(1): 338-346.

Litz, J. and G. W. Krystal (2006). "Imatinib inhibits c-Kit-induced hypoxia-inducible factor-1alpha activity and vascular endothelial growth factor expression in small cell lung cancer cells." *Mol Cancer Ther* 5(6): 1415-1422.

Ma, P., R. S. Mali, et al. (2012). "Role of intracellular tyrosines in activating KIT-induced myeloproliferative disease." *Leukemia* 26(7): 1499-1506.

Micke, P., M. Basrai, et al. (2003). "Characterization of c-kit expression in small cell lung cancer: prognostic and therapeutic implications." *Clin Cancer Res* 9(1): 188-194.

Mol, C. D., K. B. Lim, et al. (2003). "Structure of a c-kit product complex reveals the basis for kinase transactivation." *J Biol Chem* 278(34): 31461-31464.

Moutel, S., A. El Marjou, et al. (2009). "A multi-Fc-species system for recombinant antibody production." *BMC Biotechnol* 9: 14.

Orfao, A., A. C. Garcia-Montero, et al. (2007). "Recent advances in the understanding of mastocytosis: the role of KIT mutations." *Br J Haematol* 138(1): 12-30.

Orr-Urtreger, A., A. Avivi, et al. (1990). "Developmental expression of c-kit, a proto-oncogene encoded by the W locus." *Development* 109(4): 911-923.

Papayannopoulou, T., M. Brice, et al. (1991). "Isolation of c-kit receptor-expressing cells from bone marrow, peripheral blood, and fetal liver: functional properties and composite antigenic profile." *Blood* 78(6): 1403-1412.

Reshetnyak, A. V., B. Nelson, X. Shi, T. J. Boggon, A. Pavlenco, E. M. Mandel-Bausch, F. Tome, Y. Suzuki, S. S. Sidhu, I. Lax and J. Schlessinger (2013). "Structural basis for KIT receptor tyrosine kinase inhibition by antibodies targeting the D4 membrane-proximal region." Proc Natl Acad Sci USA 10(44): 17832-17837.

Roskoski, R., Jr. (2005). "Signaling by Kit protein-tyrosine kinase—the stem cell factor receptor." *Biochem Biophys Res Commun* 337(1): 1-13.

Roskoski, R., Jr. (2005). "Structure and regulation of Kit protein-tyrosine kinase—the stem cell factor receptor." *Biochem Biophys Res Commun* 338(3): 1307-1315.

Rygaard, K., T. Nakamura, et al. (1993). "Expression of the proto-oncogenes c-met and c-kit and their ligands, hepatocyte growth factor/scatter factor and stem cell factor, in SCLC cell lines and xenografts." *Br J Cancer* 67(1): 37-46.

Schittenhelm, M., O. Aichele, et al. (2003). "Complete remission of third recurrence of acute myeloid leukemia after treatment with imatinib (STI-571)." *Leuk Lymphoma* 44(7): 1251-1253.

Shi, X. and D. L. Jarvis (2007). "Protein N-glycosylation in the baculovirus-insect cell system." *Curr Drug Targets* 8(10): 1116-1125.

Shimizu, Y., L. K. Ashman, et al. (1996). "Internalization of Kit together with stem cell factor on human fetal liver-derived mast cells: new protein and RNA synthesis are required for reappearance of Kit." *J Immunol* 156(9): 3443-3449.

Theou, N., S. Tabone, et al. (2004). "High expression of both mutant and wild-type alleles of c-kit in gastrointestinal stromal tumors." *Biochim Biophys Acta* 1688(3): 250-256.

Wang, Y. Y., L. J. Zhao, et al. (2011). "C-KIT mutation cooperates with full-length AML1-ETO to induce acute myeloid leukemia in mice." *Proc Natl Acad Sci USA* 108(6): 2450-2455.

Went, P. T., S. Dirnhofer, et al. (2004). "Prevalence of KIT expression in human tumors." *J Clin Oncol* 22(22): 4514-4522.

Xiang, Z., F. Kreisel, et al. (2007). "Neoplasia driven by mutant c-KIT is mediated by intracellular, not plasma membrane, receptor signaling." *Mol Cell Biol* 27(1): 267-282.

Yee, N. S., C. W. Hsiau, et al. (1994). "Mechanism of down-regulation of c-kit receptor. Roles of receptor tyrosine kinase, phosphatidylinositol 3'-kinase, and protein kinase C." *J Biol Chem* 269(50): 31991-31998.

Yoo, J., C. H. Kim, et al. (2004). "Expression of c-kit and p53 in non-small cell lung cancers." *Cancer Res* Treat 36(3): 167-172.

Yoshida, C., A. B. Tsuji, et al. (2013). "Therapeutic efficacy of c-kit-targeted radioimmunotherapy using 90Y-labeled anti-c-kit antibodies in a mouse model of small cell lung cancer." *PLoS One* 8(3): e59248.

Yuzawa, S., Y. Opatowsky, et al. (2007). "Structural basis for activation of the receptor tyrosine kinase KIT by stem cell factor." *Cell* 130(2): 323-334.

Zhao, L., L. Qu, J. Zhou, Z. Sun, H. Zou, Y. Y. Chen, J. D. Marks and Y. Zhou (2014). "High throughput identification of monoclonal antibodies to membrane bound and secreted proteins using yeast and phage display." *PLoS One* 9(10): e111339.

Zermati, Y., P. De Sepulveda, et al. (2003). "Effect of tyrosine kinase inhibitor STI571 on the kinase activity of wild-type and various mutated c-kit receptors found in mast cell neoplasms." *Oncogene* 22(5): 660-664.

The invention claimed is:

1. An isolated human neutralizing anti-KIT antibody comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 6 in the L-CDR1 region, SEQ ID NO: 7 in the L-CDR2 region and SEQ ID NO: 8 in the L-CDR3 region.

2. The antibody of claim 1, wherein the heavy chain variable region of said antibody has the amino acid sequence set forth as SEQ ID NO: 1.

3. The antibody of claim 1, wherein the light chain variable region has the amino acid sequence set forth as SEQ ID NO: 5.

4. The antibody of claims 2 or 3, wherein the heavy chain variable region of said antibody has the amino acid sequence set forth as SEQ ID NO: 1 and the light chain variable region has the amino acid sequence set forth as SEQ ID NO: 5.

5. An isolated human neutralizing anti-KIT antibody comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 14 in the L-CDR1 region, SEQ ID NO: 15 in the L-CDR2 region and SEQ ID NO: 16 in the L-CDR3 region.

6. The antibody of claim 5, wherein the heavy chain variable region of said antibody has the amino acid sequence set forth as SEQ ID NO: 9.

7. The antibody of claim 5, wherein the light chain variable region has the amino acid sequence set forth as SEQ ID NO: 13.

8. The antibody of claim 5, wherein the heavy chain variable region of said antibody has the amino acid sequence set forth as SEQ ID NO: 9 and the light chain variable region has the amino acid sequence set forth as SEQ ID NO: 13.

9. An isolated human neutralizing anti-KIT antibody comprising a heavy chain variable region comprising SEQ ID NO: 2 in the H-CDR1 region, SEQ ID NO: 3 in the H-CDR2 region and SEQ ID NO: 4 in the H-CDR3 region; and a light chain variable region comprising SEQ ID NO: 27 in the L-CDR1 region, SEQ ID NO: 28 in the L-CDR2 region and SEQ ID NO: 29 in the L-CDR3 region.

10. The antibody of claim 9, wherein the light chain variable region has the amino acid sequence set forth as SEQ ID NO: 26.

11. The antibody of claim 9, wherein the heavy chain variable region of said antibody has the amino acid sequence set forth as SEQ ID NO: 1 and the light chain variable region has the amino acid sequence set forth as SEQ ID NO: 26.

12. An isolated human neutralizing anti-KIT antibody comprising a heavy chain variable region comprising SEQ ID NO: 10 in the H-CDR1 region, SEQ ID NO: 11 in the H-CDR2 region and SEQ ID NO: 12 in the H-CDR3 region; and a light chain variable region comprising SEQ ID NO: 31 in the L-CDR1 region, SEQ ID NO: 32 in the L-CDR2 region and SEQ ID NO: 33 in the L-CDR3 region.

13. The antibody of claim 12, wherein the light chain variable region has the amino acid sequence set forth as SEQ ID NO: 30.

14. The antibody of claim 12, wherein the heavy chain variable region of said antibody has the amino acid sequence set forth as SEQ ID NO: 9 and the light chain variable region has the amino acid sequence set forth as SEQ ID NO: 30.

* * * * *

SEQUENCE LISTING

```
<160> NUMBER OF SEQ ID NOS: 33

<210> SEQ ID NO 1
<211> LENGTH: 123
<212> TYPE: PRT
<213> ORGANISM: Artificial
<220> FEATURE:
<223> OTHER INFORMATION: Synthetic 2D1 VH chain

<400> SEQUENCE: 1

Met Ala Gln Val Lys Leu Gln Glu Ser Gly Gly Gly Leu Val Gln Pro
1               5                   10                  15

Gly Gly Ser Leu Arg Leu Ser Cys Ala Ala Ser Gly Phe Thr Phe Asp
            20                  25                  30

Ser Tyr Ala Met Ser Trp Val Arg Gln Ala Pro Gly Lys Gly Leu Glu
        35                  40                  45
```

-continued

```
Trp Val Ser Tyr Ile Thr Ser Ser Ser Ser Thr Ile Tyr Tyr Val Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Asp Glu Asp Thr Ala Val Tyr
                85                  90                  95

Tyr Cys Ala Arg Leu Arg Asn Ser Glu Gly Tyr Trp Tyr Phe Asp Leu
            100                 105                 110

Trp Gly Arg Gly Thr Leu Val Thr Val Ser Ser
        115                 120


<210> SEQ ID NO 2
<211> LENGTH: 8
<212> TYPE: PRT
<213> ORGANISM: Artificial
<220> FEATURE:
<223> OTHER INFORMATION: Synthetic 2D1 H-CDR1

<400> SEQUENCE: 2

Gly Phe Thr Phe Asp Ser Tyr Ala
1               5


<210> SEQ ID NO 3
<211> LENGTH: 8
<212> TYPE: PRT
<213> ORGANISM: Artificial
<220> FEATURE:
<223> OTHER INFORMATION: Synthetic 2D1 H-CDR2

<400> SEQUENCE: 3

Ile Thr Ser Ser Ser Ser Thr Ile
1               5


<210> SEQ ID NO 4
<211> LENGTH: 13
<212> TYPE: PRT
<213> ORGANISM: Artificial
<220> FEATURE:
<223> OTHER INFORMATION: Synthetic 2 D1 H-CDR3

<400> SEQUENCE: 4

Arg Leu Arg Asn Ser Glu Gly Tyr Trp Tyr Phe Asp Leu
1               5                   10


<210> SEQ ID NO 5
<211> LENGTH: 110
<212> TYPE: PRT
<213> ORGANISM: Artificial
<220> FEATURE:
<223> OTHER INFORMATION: Synthetic 2D1 VL chain

<400> SEQUENCE: 5

Ser Gln Ser Ala Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Phe
            20                  25                  30

Ala Ser Trp Tyr Gln Gln Lys Pro Gly Gln Ala Pro Leu Leu Val Met
        35                  40                  45

Tyr Gly Gln Asn Ile Arg Pro Ser Gly Ile Pro Asp Arg Phe Ser Gly
    50                  55                  60

Ser Ser Ser Gly Asn Ser Ala Ser Leu Thr Ile Thr Gly Ala Gln Ala
65                  70                  75                  80
```

```
Glu Asp Glu Ala Asp Tyr Tyr Cys Asn Ser Arg Asp Ser Ser Tyr Asn
                85                  90                  95

His Trp Val Phe Gly Gly Gly Thr Lys Leu Thr Val Leu Gly
            100                 105                 110


<210> SEQ ID NO 6
<211> LENGTH: 6
<212> TYPE: PRT
<213> ORGANISM: Artificial
<220> FEATURE:
<223> OTHER INFORMATION: Synthetic 2D1 L-CDR1

<400> SEQUENCE: 6

Ser Leu Arg Ser Tyr Phe
1               5


<210> SEQ ID NO 7
<211> LENGTH: 3
<212> TYPE: PRT
<213> ORGANISM: Artificial
<220> FEATURE:
<223> OTHER INFORMATION: Synthetic 2D1 L-CDR2

<400> SEQUENCE: 7

Gly Gln Asn
1


<210> SEQ ID NO 8
<211> LENGTH: 11
<212> TYPE: PRT
<213> ORGANISM: Artificial
<220> FEATURE:
<223> OTHER INFORMATION: Synthetic 2D1 L-CDR3

<400> SEQUENCE: 8

Asn Ser Arg Asp Ser Ser Tyr Asn His Trp Val
1               5                   10


<210> SEQ ID NO 9
<211> LENGTH: 124
<212> TYPE: PRT
<213> ORGANISM: Artificial
<220> FEATURE:
<223> OTHER INFORMATION: Synthetic 3G1 VH chain

<400> SEQUENCE: 9

Met Ala Gln Val Gln Leu Val Glu Ser Trp Gly Gly Val Ala Gln Pro
1               5                   10                  15

Gly Arg Ser Leu Arg Leu Ser Cys Ala Ala Ser Gly Phe Thr Phe Ser
            20                  25                  30

Ser Phe Ala Met His Trp Val Arg Gln Ala Pro Gly Lys Gly Leu Glu
        35                  40                  45

Trp Val Ala Val Thr Ser Tyr Asp Gly Ser Asn Glu Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ala Met Val Arg Gly Val Thr Phe Gly Asp Leu Asp
            100                 105                 110

Tyr Trp Gly Gln Gly Thr Leu Val Thr Val Ser Ser
        115                 120
```

<210> SEQ ID NO 10
<211> LENGTH: 8
<212> TYPE: PRT
<213> ORGANISM: Artificial
<220> FEATURE:
<223> OTHER INFORMATION: Synthetic 3G1 H-CDR1

<400> SEQUENCE: 10

```
Gly Phe Thr Phe Ser Ser Phe Ala
1               5
```

<210> SEQ ID NO 11
<211> LENGTH: 8
<212> TYPE: PRT
<213> ORGANISM: Artificial
<220> FEATURE:
<223> OTHER INFORMATION: Synthetic 3G1 H-CDR2

<400> SEQUENCE: 11

```
Thr Ser Tyr Asp Gly Ser Asn Glu
1               5
```

<210> SEQ ID NO 12
<211> LENGTH: 15
<212> TYPE: PRT
<213> ORGANISM: Artificial
<220> FEATURE:
<223> OTHER INFORMATION: Synthetic 3G1 H-CDR3

<400> SEQUENCE: 12

```
Ala Lys Ala Met Val Arg Gly Val Thr Phe Gly Asp Leu Asp Tyr
1               5                   10                  15
```

<210> SEQ ID NO 13
<211> LENGTH: 110
<212> TYPE: PRT
<213> ORGANISM: Artificial
<220> FEATURE:
<223> OTHER INFORMATION: Synthetic 3G1 VL chain

<400> SEQUENCE: 13

```
Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Glu Gln Ala Pro Val Leu Val Ile Tyr
        35                  40                  45

Gly Glu Asn Ser Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr His
                85                  90                  95

Leu Arg Val Phe Gly Gly Gly Thr Lys Leu Thr Val Leu Gly
            100                 105                 110
```

<210> SEQ ID NO 14
<211> LENGTH: 6
<212> TYPE: PRT
<213> ORGANISM: Artificial
<220> FEATURE:
<223> OTHER INFORMATION: Synthetic 3G1 L-CDR1

<400> SEQUENCE: 14

Ser Leu Arg Ser Tyr Tyr
1 5

<210> SEQ ID NO 15
<211> LENGTH: 3
<212> TYPE: PRT
<213> ORGANISM: Artificial
<220> FEATURE:
<223> OTHER INFORMATION: Synthetic 3G1 L-CDR2

<400> SEQUENCE: 15

Gly Glu Asn
1

<210> SEQ ID NO 16
<211> LENGTH: 12
<212> TYPE: PRT
<213> ORGANISM: Artificial
<220> FEATURE:
<223> OTHER INFORMATION: Synthetic 3G1 L-CDR3

<400> SEQUENCE: 16

Asn Ser Arg Asp Ser Ser Gly Thr His Leu Arg Val
1 5 10

<210> SEQ ID NO 17
<211> LENGTH: 247
<212> TYPE: PRT
<213> ORGANISM: Artificial
<220> FEATURE:
<223> OTHER INFORMATION: Synthetic 2D1 VH-linker-VL

<400> SEQUENCE: 17

Met Ala Gln Val Lys Leu Gln Glu Ser Gly Gly Gly Leu Val Gln Pro
1 5 10 15

Gly Gly Ser Leu Arg Leu Ser Cys Ala Ala Ser Gly Phe Thr Phe Asp
20 25 30

Ser Tyr Ala Met Ser Trp Val Arg Gln Ala Pro Gly Lys Gly Leu Glu
35 40 45

Trp Val Ser Tyr Ile Thr Ser Ser Ser Ser Thr Ile Tyr Tyr Val Asp
50 55 60

Ser Val Lys Gly Arg Phe Thr Ile Ser Arg Asp Asn Ala Lys Asn Ser
65 70 75 80

Leu Tyr Leu Gln Met Asn Ser Leu Arg Asp Glu Asp Thr Ala Val Tyr
85 90 95

Tyr Cys Ala Arg Leu Arg Asn Ser Glu Gly Tyr Trp Tyr Phe Asp Leu
100 105 110

Trp Gly Arg Gly Thr Leu Val Thr Val Ser Ser Gly Gly Gly Gly Ser
115 120 125

Gly Gly Gly Gly Ser Gly Gly Gly Gly Ser Gln Ser Ala Leu Thr Gln
130 135 140

Asp Pro Ala Val Ser Val Ala Leu Gly Gln Thr Val Arg Ile Thr Cys
145 150 155 160

Gln Gly Asp Ser Leu Arg Ser Tyr Phe Ala Ser Trp Tyr Gln Gln Lys
165 170 175

Pro Gly Gln Ala Pro Leu Leu Val Met Tyr Gly Gln Asn Ile Arg Pro
180 185 190

```
Ser Gly Ile Pro Asp Arg Phe Ser Gly Ser Ser Ser Gly Asn Ser Ala
        195                 200                 205

Ser Leu Thr Ile Thr Gly Ala Gln Ala Glu Asp Glu Ala Asp Tyr Tyr
    210                 215                 220

Cys Asn Ser Arg Asp Ser Ser Tyr Asn His Trp Val Phe Gly Gly Gly
225                 230                 235                 240

Thr Lys Leu Thr Val Leu Gly
                245


<210> SEQ ID NO 18
<211> LENGTH: 248
<212> TYPE: PRT
<213> ORGANISM: Artificial
<220> FEATURE:
<223> OTHER INFORMATION: Synthetic 3G1 VH-linker-VL

<400> SEQUENCE: 18

Met Ala Gln Val Gln Leu Val Glu Ser Trp Gly Gly Val Ala Gln Pro
1               5                   10                  15

Gly Arg Ser Leu Arg Leu Ser Cys Ala Ala Ser Gly Phe Thr Phe Ser
            20                  25                  30

Ser Phe Ala Met His Trp Val Arg Gln Ala Pro Gly Lys Gly Leu Glu
        35                  40                  45

Trp Val Ala Val Thr Ser Tyr Asp Gly Ser Asn Glu Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Lys Ala Met Val Arg Gly Val Thr Phe Gly Asp Leu Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Ser Glu Leu Thr Gln
    130                 135                 140

Asp Pro Ala Val Ser Val Ala Leu Gly Gln Thr Val Arg Ile Thr Cys
145                 150                 155                 160

Gln Gly Asp Ser Leu Arg Ser Tyr Tyr Ala Ser Trp Tyr Gln Gln Lys
                165                 170                 175

Pro Glu Gln Ala Pro Val Leu Val Ile Tyr Gly Glu Asn Ser Arg Pro
            180                 185                 190

Ser Gly Ile Pro Asp Arg Phe Ser Gly Ser Ser Ser Gly Asn Thr Ala
        195                 200                 205

Ser Leu Thr Ile Thr Gly Ala Gln Ala Glu Asp Glu Ala Asp Tyr Tyr
    210                 215                 220

Cys Asn Ser Arg Asp Ser Ser Gly Thr His Leu Arg Val Phe Gly Gly
225                 230                 235                 240

Gly Thr Lys Leu Thr Val Leu Gly
                245


<210> SEQ ID NO 19
<211> LENGTH: 369
<212> TYPE: DNA
<213> ORGANISM: Artificial
<220> FEATURE:
<223> OTHER INFORMATION: Synthetic 2D1 VH chain
```

<400> SEQUENCE: 19
atggcccagg tcaagctgca ggagtctggg ggaggcttgg tacagcctgg ggggtccctg 60
agactctcct gtgcagcctc tggattcacc tttgacagct atgccatgag ctgggtccgc 120
caggctccag ggaaggggct ggagtgggtt tcatacatta ctagtagtag tagtaccata 180
tactacgtag actctgtgaa gggccgattc accatctcca gagacaatgc caagaactca 240
ctgtatctgc aaatgaacag cctgagagac gaggacacgg ctgtgtatta ctgtgcgaga 300
ctccgtaact ccgagggata ctggtacttc gatctctggg gccgtggcac cctggtcacc 360
gtctcctca 369

<210> SEQ ID NO 20
<211> LENGTH: 330
<212> TYPE: DNA
<213> ORGANISM: Artificial
<220> FEATURE:
<223> OTHER INFORMATION: Synthetic 2D1 VL chain

<400> SEQUENCE: 20
tcgcagtctg ctctgactca ggaccctgct gtgtctgtgg ccttgggaca gacagtcagg 60
atcacatgcc aaggagacag cctcagaagc tattttgcaa gttggtacca gcagaagcca 120
ggacaggccc ctctccttgt catgtatggt caaaacatcc ggccctcagg gatcccagac 180
cgattctctg gctccagctc aggaaactca gcttccttga ccatcactgg ggctcaggcg 240
gaagatgagg ctgactatta ctgtaactcc cgggacagca gttataacca ttgggtgttc 300
ggcggaggga ccaagctgac cgtcctaggt 330

<210> SEQ ID NO 21
<211> LENGTH: 741
<212> TYPE: DNA
<213> ORGANISM: Artificial
<220> FEATURE:
<223> OTHER INFORMATION: Synthetic 2D1 VH-linker-VL

<400> SEQUENCE: 21
atggcccagg tcaagctgca ggagtctggg ggaggcttgg tacagcctgg ggggtccctg 60
agactctcct gtgcagcctc tggattcacc tttgacagct atgccatgag ctgggtccgc 120
caggctccag ggaaggggct ggagtgggtt tcatacatta ctagtagtag tagtaccata 180
tactacgtag actctgtgaa gggccgattc accatctcca gagacaatgc caagaactca 240
ctgtatctgc aaatgaacag cctgagagac gaggacacgg ctgtgtatta ctgtgcgaga 300
ctccgtaact ccgagggata ctggtacttc gatctctggg gccgtggcac cctggtcacc 360
gtctcctcag gtggaggcgg ttcaggcgga ggtggctctg gcggtggcgg atcgcagtct 420
gctctgactc aggaccctgc tgtgtctgtg gccttgggac agacagtcag gatcacatgc 480
caaggagaca gcctcagaag ctattttgca agttggtacc agcagaagcc aggacaggcc 540
cctctccttg tcatgtatgg tcaaaacatc cggccctcag ggatcccaga ccgattctct 600
ggctccagct caggaaactc agcttccttg accatcactg gggctcaggc ggaagatgag 660
gctgactatt actgtaactc ccgggacagc agttataacc attgggtgtt cggcggaggg 720
accaagctga ccgtcctagg t 741

<210> SEQ ID NO 22
<211> LENGTH: 372
<212> TYPE: DNA
<213> ORGANISM: Artificial

<220> FEATURE:
<223> OTHER INFORMATION: Synthetic 3G1 VH chain

<400> SEQUENCE: 22

```
atggcccagg tgcagctggt ggagtcttgg ggaggcgtgg cccagcctgg gaggtccctg     60

agactctcct gtgcagcctc tggattcacc ttcagtagtt ttgccatgca ctgggtccgc    120

caggctccag gcaaggggct ggagtgggtg gcagttacat catatgatgg aagtaatgaa    180

tactatgcag actccgtgaa gggccgattc accatctcca gagacaattc caagaacacg    240

ctgtatctgc aaatgaacag cctgagagct gaggacacgg ctgtgtatta ctgtgcgaaa    300

gctatggttc ggggagttac gtttggcgac cttgactact ggggccaggg aaccctggtc    360

accgtctcct ca                                                        372
```

<210> SEQ ID NO 23
<211> LENGTH: 330
<212> TYPE: DNA
<213> ORGANISM: Artificial
<220> FEATURE:
<223> OTHER INFORMATION: Synthetic 3G1 VL chain

<400> SEQUENCE: 23

```
tcgtctgagc tgactcagga ccctgctgtg tctgtggcct tgggacagac agtcagaatc     60

acatgccaag gagacagcct cagaagttat tatgcaagct ggtaccagca gaagccagaa    120

caggcccctg tacttgtcat ctatggtgaa aacagccggc cctcagggat cccagaccga    180

ttctctggct ccagctcagg aaacacagct tccttgacca tcactggggc tcaggcggaa    240

gatgaggctg actattactg caactctcgc gacagcagtg gtacccatct aagggtattc    300

ggcggaggga ccaagctgac cgtcctaggt                                     330
```

<210> SEQ ID NO 24
<211> LENGTH: 744
<212> TYPE: DNA
<213> ORGANISM: Artificial
<220> FEATURE:
<223> OTHER INFORMATION: Synthetic 3G1 VH-linker-VL

<400> SEQUENCE: 24

```
atggcccagg tgcagctggt ggagtcttgg ggaggcgtgg cccagcctgg gaggtccctg     60

agactctcct gtgcagcctc tggattcacc ttcagtagtt ttgccatgca ctgggtccgc    120

caggctccag gcaaggggct ggagtgggtg gcagttacat catatgatgg aagtaatgaa    180

tactatgcag actccgtgaa gggccgattc accatctcca gagacaattc caagaacacg    240

ctgtatctgc aaatgaacag cctgagagct gaggacacgg ctgtgtatta ctgtgcgaaa    300

gctatggttc ggggagttac gtttggcgac cttgactact ggggccaggg aaccctggtc    360

accgtctcct caggtggagg cggttcaggc ggaggtggct ctggcggtgg cggatcgtct    420

gagctgactc aggaccctgc tgtgtctgtg gccttgggac agacagtcag aatcacatgc    480

caaggagaca gcctcagaag ttattatgca agctggtacc agcagaagcc agaacaggcc    540

cctgtacttg tcatctatgg tgaaaacagc cggccctcag ggatcccaga ccgattctct    600

ggctccagct caggaaacac agcttccttg accatcactg gggctcaggc ggaagatgag    660

gctgactatt actgcaactc tcgcgacagc agtggtaccc atctaagggt attcggcgga    720

gggaccaagc tgaccgtcct aggt                                           744
```

```
<210> SEQ ID NO 25
<211> LENGTH: 106
<212> TYPE: PRT
<213> ORGANISM: Homo sapiens

<400> SEQUENCE: 25

Asn Lys Pro Glu Ile Leu Thr Tyr Asp Arg Leu Val Asn Gly Met Leu
1               5                   10                  15

Gln Cys Val Ala Ala Gly Phe Pro Glu Pro Thr Ile Asp Trp Tyr Phe
            20                  25                  30

Cys Pro Gly Thr Glu Gln Arg Cys Ser Ala Ser Val Leu Pro Val Asp
        35                  40                  45

Val Gln Thr Leu Asn Ser Ser Gly Pro Pro Phe Gly Lys Leu Val Val
    50                  55                  60

Gln Ser Ser Ile Asp Ser Ser Ala Phe Lys His Asn Gly Thr Val Glu
65                  70                  75                  80

Cys Lys Ala Tyr Asn Asp Val Gly Lys Thr Ser Ala Tyr Phe Asn Phe
                85                  90                  95

Ala Phe Lys Glu Gln Ile His Pro His Thr
            100                 105


<210> SEQ ID NO 26
<211> LENGTH: 112
<212> TYPE: PRT
<213> ORGANISM: Artificial
<220> FEATURE:
<223> OTHER INFORMATION: Synthetic 2D1-C7 VL chain

<400> SEQUENCE: 26

Ser Gln Ser Val Leu Thr Gln Asp Pro Ala Val Ser Val Ala Leu Gly
1               5                   10                  15

Gln Thr Val Arg Ile Thr Cys Gln Gly Asp Ser Leu Arg Ser Tyr Tyr
            20                  25                  30

Ala Ser Trp Tyr Gln Gln Lys Pro Gly Gln Ala Pro Leu Leu Val Met
        35                  40                  45

Tyr Gly Glu Asn Ile Arg Pro Ser Gly Ile Pro Asp Arg Phe Ser Gly
    50                  55                  60

Ser Thr Ser Gly Asn Ser Ala Ser Leu Thr Ile Thr Gly Ala Gln Ala
65                  70                  75                  80

Glu Asp Glu Ala Asp Tyr Tyr Cys Asn Ser Arg Asp Ser Ser Gly Asn
                85                  90                  95

His Leu Asn Trp Val Phe Gly Gly Gly Thr Lys Leu Thr Val Leu Gly
            100                 105                 110


<210> SEQ ID NO 27
<211> LENGTH: 6
<212> TYPE: PRT
<213> ORGANISM: Artificial
<220> FEATURE:
<223> OTHER INFORMATION: Synthetic 2D1-C7 L-CDR1

<400> SEQUENCE: 27

Ser Leu Arg Ser Tyr Tyr
1               5


<210> SEQ ID NO 28
<211> LENGTH: 3
<212> TYPE: PRT
<213> ORGANISM: Artificial
<220> FEATURE:
<223> OTHER INFORMATION: Synthetic 2D1-C7 L-CDR2
```

<400> SEQUENCE: 28

Gly Glu Asn
1

<210> SEQ ID NO 29
<211> LENGTH: 13
<212> TYPE: PRT
<213> ORGANISM: Artificial
<220> FEATURE:
<223> OTHER INFORMATION: Synthetic 2D1-C7 L-CDR3

<400> SEQUENCE: 29

Asn Ser Arg Asp Ser Ser Gly Asn His Leu Asn Trp Val
1               5                   10

<210> SEQ ID NO 30
<211> LENGTH: 109
<212> TYPE: PRT
<213> ORGANISM: Artificial
<220> FEATURE:
<223> OTHER INFORMATION: Synthetic 3G1-A2 VL chain

<400> SEQUENCE: 30

Ser Ser Glu Leu Thr Gln Asp Pro Ala Val Ser Val Ala Leu Gly Gln
1               5                   10                  15

Thr Val Arg Lys Thr Cys Gln Gly Asp Ser Leu Lys Ser Tyr Tyr Ala
            20                  25                  30

Ser Trp Tyr Gln Gln Lys Pro Gly Gln Ala Pro Val Leu Val Ile Tyr
        35                  40                  45

Gly Glu Asn Ser Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Cys Ser Arg Ala Thr Gly Gly Tyr His
                85                  90                  95

Arg Ile Phe Gly Gly Gly Thr Lys Leu Thr Val Leu Gly
            100                 105

<210> SEQ ID NO 31
<211> LENGTH: 6
<212> TYPE: PRT
<213> ORGANISM: Artificial
<220> FEATURE:
<223> OTHER INFORMATION: Synthetic 3G1-A2 L-CDR1

<400> SEQUENCE: 31

Ser Leu Lys Ser Tyr Tyr
1               5

<210> SEQ ID NO 32
<211> LENGTH: 3
<212> TYPE: PRT
<213> ORGANISM: Artificial
<220> FEATURE:
<223> OTHER INFORMATION: Synthetic 3G1-A2 L-CDR2

<400> SEQUENCE: 32

Gly Glu Asn
1

-continued

```
<210> SEQ ID NO 33
<211> LENGTH: 11
<212> TYPE: PRT
<213> ORGANISM: Artificial
<220> FEATURE:
<223> OTHER INFORMATION: Synthetic 3G1-A2 L-CDR3

<400> SEQUENCE: 33

Cys Ser Arg Ala Thr Gly Gly Tyr His Arg Ile
1               5                   10
```